United States Patent
Robey et al.

(10) Patent No.: US 10,940,241 B2
(45) Date of Patent: Mar. 9, 2021

(54) FORMATION OF STABLE CARTILAGE

(71) Applicants: The United States of America, as represented by the Secretary, Department of Health and Human Services, Bethesda, MD (US); Hadasit Medical Research Services and Development Ltd., Jerusalem (IL); Mitchell Shirvan, Kfar Saba (IL)

(72) Inventors: Pamela Gehron Robey, Bethesda, MD (US); Sergei Kuznetsov, Rockville, MD (US); Raphael Gorodetsky, Jerusalem (IL); Astar Hailu-Lazmi, Jerusalem (IL); Mitchell Shirvan, Kfar Saba (IL); Joseph Featherall, Cleveland, OH (US)

(73) Assignees: The United States of America, as represented by the Secretary, Department of Health and Human Services, Bethesda, MD (US); Hadasit Medical Research Services and Development Ltd., Jerusalem (IL)

(*) Notice: Subject to any disclaimer, the term of this patent is extended or adjusted under 35 U.S.C. 154(b) by 0 days.

(21) Appl. No.: 16/616,418

(22) PCT Filed: May 31, 2018

(86) PCT No.: PCT/US2018/035448
§ 371 (c)(1),
(2) Date: Nov. 22, 2019

(87) PCT Pub. No.: WO2018/222906
PCT Pub. Date: Dec. 6, 2018

(65) Prior Publication Data
US 2020/0171215 A1 Jun. 4, 2020

Related U.S. Application Data

(60) Provisional application No. 62/513,874, filed on Jun. 1, 2017.

(51) Int. Cl.
*A61L 31/16* (2006.01)
*A61L 31/04* (2006.01)
*A61K 45/06* (2006.01)

(52) U.S. Cl.
CPC ............ *A61L 31/16* (2013.01); *A61L 31/042* (2013.01); *A61L 31/046* (2013.01); *A61K 45/06* (2013.01);
(Continued)

(58) Field of Classification Search
None
See application file for complete search history.

(56) References Cited

U.S. PATENT DOCUMENTS 6,150,505 A 11/2000 Marx et al.
6,503,731 B2 1/2003 Marx et al.
(Continued)

FOREIGN PATENT DOCUMENTS

WO WO 2014/110353 A1 6/2014

OTHER PUBLICATIONS

Featherall et al., "In vivo formation of stable hyaline cartilage by transplantation of naive human bone marrow stromal cells," *Osteoarthritis and Cartilage* 26 (Supplement 1), 2 pages, (Apr. 1, 2018).
(Continued)

*Primary Examiner* — Katherine Peebles
*Assistant Examiner* — Casey S Hagopian
(74) *Attorney, Agent, or Firm* — Klarquist Sparkman, LLP

(57) ABSTRACT

Methods are provided for promoting cartilage growth and/or repair. The methods include, administering locally to a site in a subject in need thereof, bone marrow stromal cells attached to fibrin microbeads comprising crosslinked hyaluronic acid and thereby producing stable cartilage locally at the site in the subject.

27 Claims, 12 Drawing Sheets

| Group | Vehicles | Recipient mouse strain | Harvest times (weeks) | # recovered/ total # | Bone scores (ave) | Cartilage scores (ave) |
|---|---|---|---|---|---|---|
| 1 | FMBs | 5 NSG | 19 | 5/5 (Fig. 1C,E,F) | 3,2,3,1,2 (2.2±0.8) | 2,0,0,2,2 (1.2±1.1) |
|  | HyA-FMBs |  | 19 | 5/5 (Fig. 1D,G,H) | 3,3,3,3,3 (3.0±0.0)$^{ns}$ | 2,3,3,4,3 (3.0±0.7)* |

(52) U.S. Cl.
CPC ....... *A61L 2400/06* (2013.01); *A61L 2430/06* (2013.01)

(56) References Cited

U.S. PATENT DOCUMENTS

| | | | |
|---|---|---|---|
| 6,552,172 | B2 | 4/2003 | Marx et al. |
| 9,125,743 | B2 | 9/2015 | Chen et al. |
| 2003/0045690 | A1 | 3/2003 | Marx |
| 2012/0207715 | A1* | 8/2012 | Gorodetsky ......... C12N 5/0075 424/93.7 |

OTHER PUBLICATIONS

Ferris et al., "In vivo healing of meniscal lacerations using bone marrow-derived mesenchymal stem cells and fibrin glue," *Stem Cells International* 2012: pages (E-pub Jan. 16, 2012).

International Search Report and Written Opinion from parent PCT Application No. PCT/US2018/035448, 15 pages (dated Sep. 20, 2018).

Kim et al., "Synthesis and characterization of hyaluronic acid micro-bead and hydrogel implant crosslinked by divinyl sulfone," *18th International Conference on Composite Materials* 4 pages (downloaded Jun. 22, 2017).

Kuznetsov et al., "In vivo formation of bone and haematopoietic territories by transplanted human bone marrow stromal cells generated in medium with and without osteogenic supplements," *Journal of Tissue Engineering and Regenerative Medicine* 7(3): 226-235 (Mar. 2013).

Scotti et al., "Engineering of a functional bone organ through endochondral ossification," *PNAS* 110(10):3997-4002 (2013).

Serafini et al., "Establishment of bone marrow and hematopoietic niches in vivo by reversion of chondrocyte differentiation of human bone marrow stromal cells," *Stem Cell Res.* 12(3):659-72 (2014).

Snyder et al., "A fibrin/hyaluronic acid hydrogel for the delivery of mesenchymal stem cells and potential for articular cartilage repair," *J. Bio. Eng.* 8(10):1-11 (2014).

* cited by examiner naïve BMSCs → FMBs / HyA-FMB → subcutaneous transplant into immunocompromised mice FMBs or HyA-FMBs alone (empty)

| Group | Vehicles | Recipient mouse strain | Harvest times (weeks) | # recovered/ total # | Bone scores (ave) | Cartilage scores (ave) |
|---|---|---|---|---|---|---|
| 1 | FMBs | 5 NSG | 19 | 5/5 (Fig. 1C,E,F) | 3,2,3,1,2 (2.2±0.8) | 2,0,0,2,2 (1.2±1.1) |
|   | HyA-FMBs |   | 19 | 5/5 (Fig. 1D,G,H) | 3,3,3,3,3 (3.0±0.0)ns | 2,3,3,4,3 (3.0±0.7)* |

FMBs FIG. 1C

HyA-FMBs FIG. 1D

FMBs – NSG
19 wks FIG. 1E
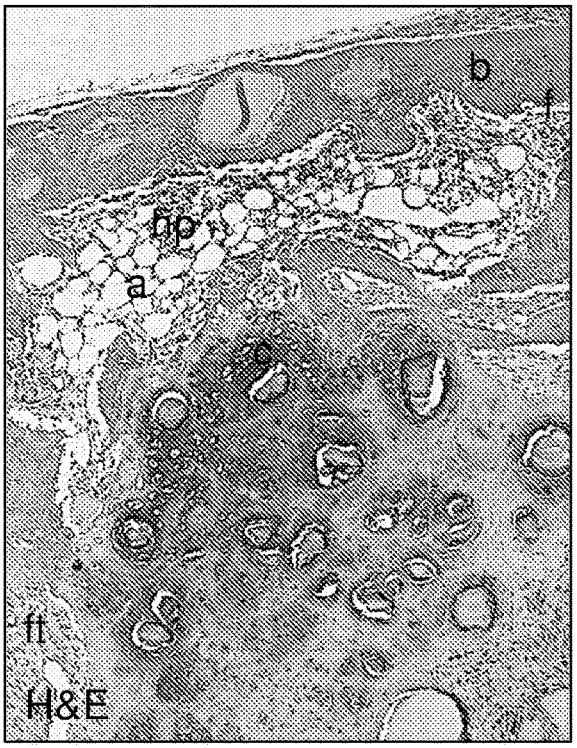
H&E
FMBs – NSG
19 wks FIG. 1F
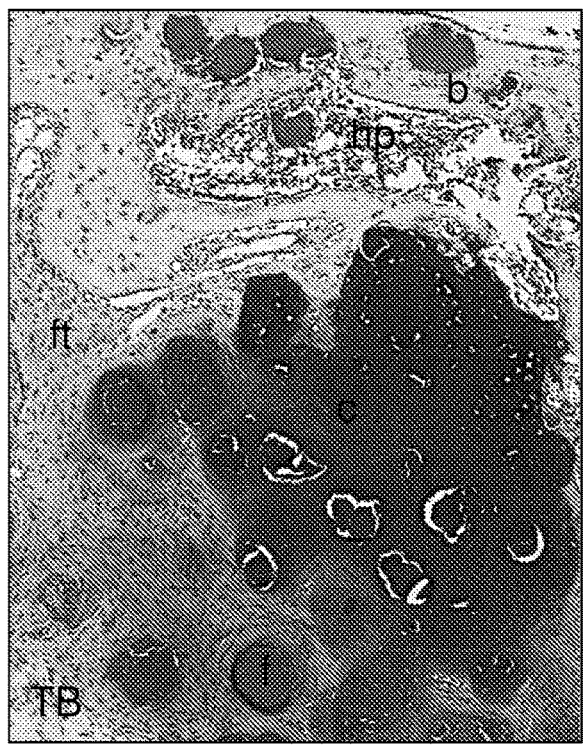
TB
HyA-FMBs – NSG
19 wks FIG. 1G
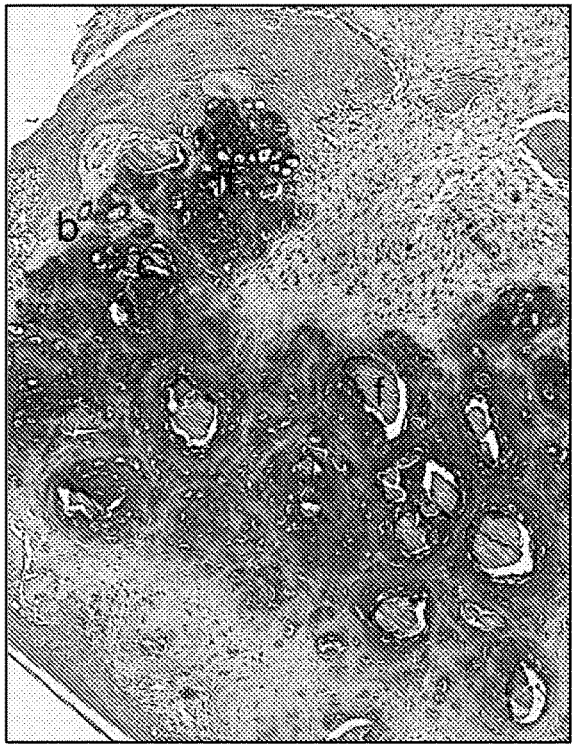
H&E
HyA-FMBs – NSG
19 wks FIG. 1H
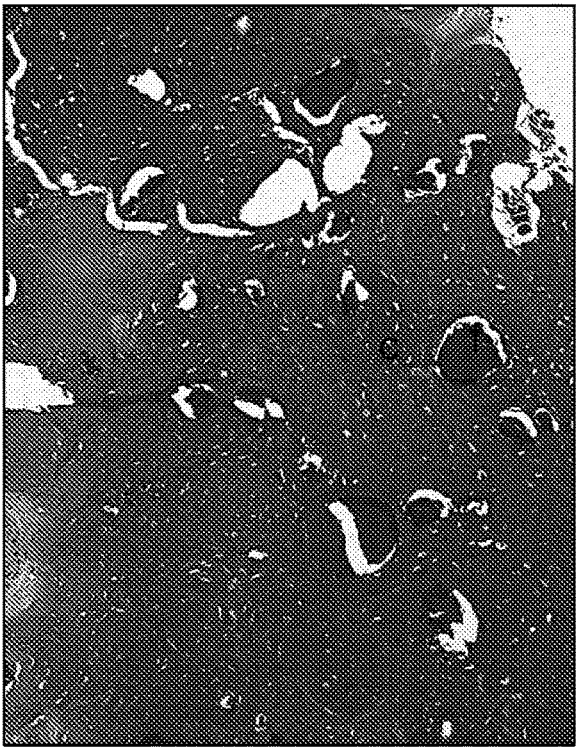
TB

FIG. 2

| Group | Vehicles | Recipient mouse strain | Harvest times (weeks) | # recovered/ total # | Bone scores | Cartilage scores |
|---|---|---|---|---|---|---|
| 2 | HyA-FMBs | 4 NSG | 8 | 2/2 (Fig. 3A,B,E,F) | 1,2 | 2,3 |
| | | | 16 | 1/1 (Fig 4A,B,D,E,F) | 1 | 3 |
| | | | 28 | 1/1 (Fig. 5A,B,E, G,H) | 2 | 3 |
| | Empty FMBs | | 8 | 0/1 | 0 | 0 |
| | | | 16 | 0/1 | 0 | 0 |
| | Empty HyA-FMBs | | 8 | 1/1 (Fig. 3D) | 0 | 0 |
| | | | 16 | 0/1 | 0 | 0 |
| | HyA-FMBs | 4 SHC | 8 | 2/2 (Fig. 3C) | 0,0 | 1,1 |
| | | | 16 | 1/1 (Fig. 4C) | 1 | 2 |
| | | | 28 | 1/1 (Fig. 5C,D,F) | 1 | 4 |

HyA-FMBs – NSG
8 wks

HyA-FMBs – NSG
8 wks

HyA-FMBs – SHC
8 wk

Empty HyA-FMBs – NSG
8 wk

HyA-FMBs – NSG
8 wks

Anti-COL X

HyA-FMBs – NSG
8 wks

Isotype control

HyA-FMBs – NSG
16 wks

HyA-FMBs – NSG
16 wks

HyA-FMBs – SHC
16 wks

HyA-FMBs – NSG
16 wks

HyA-FMBs – NSG
16 wks

HyA-FMBs – NSG
16 wks

HyA-FMBs – NSG
28 wks  FIG. 5A
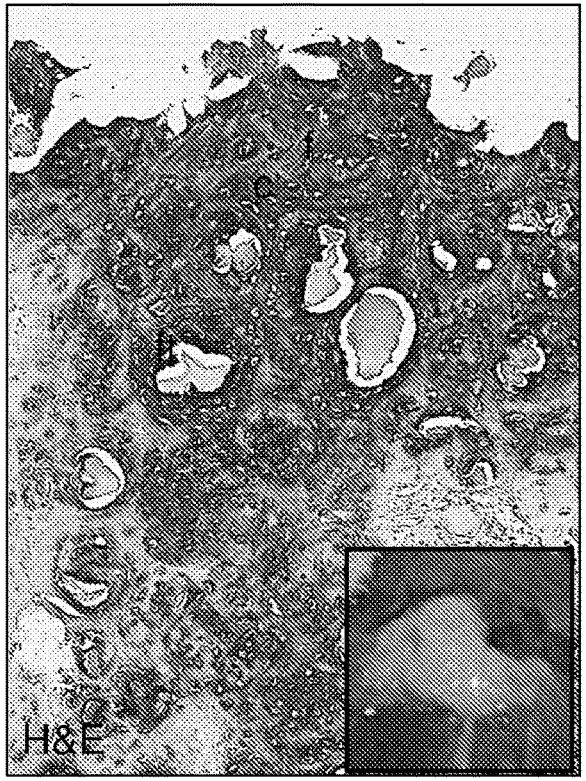
HyA-FMBs – NSG
28 wks  FIG. 5B
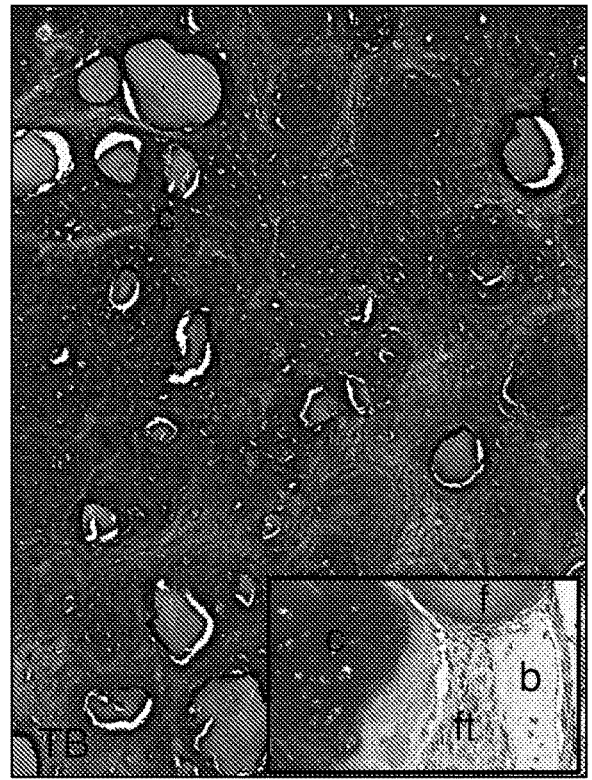
HyA-FMBs – SHC
28 wks  FIG. 5C
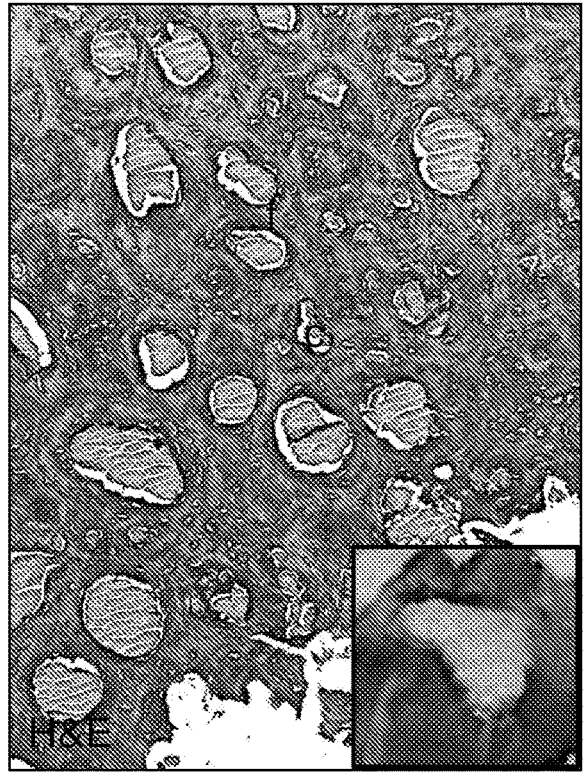
HyA-FMBs – SHC
28 wks  FIG. 5D

HyA-FMBs – NSG
28 wks

Anti-COL II

HyA-FMBs – SHC
28 wks

Anti-COL X

HyA-FMBs – NSG
28 wks

Anti-Human Mitochondria

HyA-FMBs – NSG
28 wks

Isotype Control

FIG. 6A
FIG. 6C
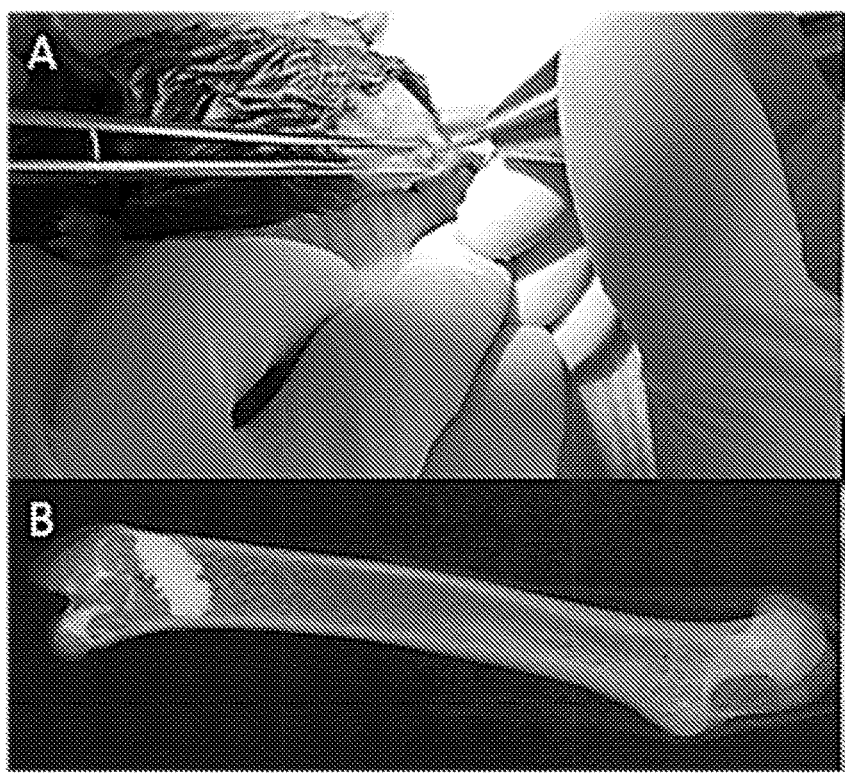
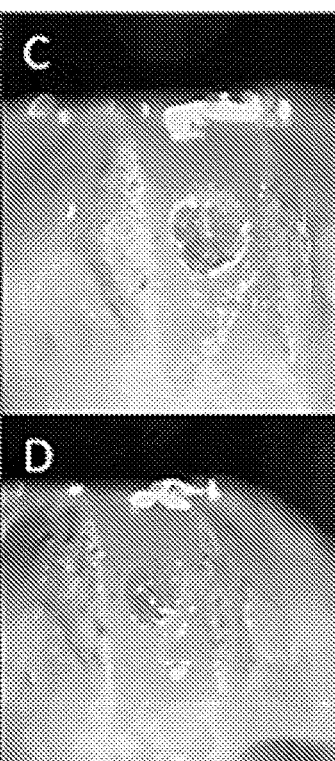
FIG. 6B
FIG. 6D

FORMATION OF STABLE CARTILAGE

CROSS REFERENCE TO RELATED APPLICATION

This is a § 371 U.S. national stage of International Application No. PCT/US2018/035448, filed May 31, 2018, which claims the benefit of U.S. Provisional Application No. 62/513,874, filed Jun. 1, 2017, which is herein incorporated by reference in its entirety.

FIELD

The present disclosure pertains to the field of cartilage injury and disease and methods of treating, alleviating, or preventing the same.

BACKGROUND

Osteoarthritis (OA) and other degenerative diseases of cartilage affect ~50% of the population over the age of 65 years. However, these defects never heal on their own. Medicinal and surgical approaches are often ineffective. They have a major impact on the ability to work and quality of life, making these conditions a major social issue. Medicinal treatments are only palliative, and surgical interventions (mosaicplasty, microfracture, transplantation of autologous chondrocytes) often do not achieve optimal outcomes. Successful tissue engineering using transplantation of autologous chondrocytes is also limited. Bone marrow stromal cells (BMSCs, also known as bone marrow-derived mesenchymal stem cells), have been suggested to be a good source of cells for cartilage reconstruction. However, studies using BMSCs pre-differentiated into cartilage prior to transplantation failed to demonstrate formation of stable, hyaline-like cartilage that was resistant to hypertrophy in vivo. A need remains for methods that utilize BMSC to form stable cartilage in vivo, so that these cells can be used to repair and regrow cartilage in situ.

There is a need in the art for methods of a method of repairing and regrowth of cartilage in vivo.

SUMMARY

Studies have transplanted BMSCs, pre-differentiated into a chondrogenic phenotype, with different scaffolds. However, to date, no procedures have resulted in formation of stable, hyaline-like cartilage, resistant to hypertrophic mineralization (Pelttari et al. Arthritis & Rheumatism. 2006; 54(10):3254-66). Thus, prior to the present disclosure, naïve (undifferentiated) bone marrow stromal cells have not been used for the successful production of stable cartilage in vivo.

Provided herein are methods for promoting cartilage growth and/or repair locally in a subject. The methods include administering locally to a site in a subject in need thereof, naïve bone marrow stromal cells attached to fibrin microbeads comprising crosslinked hyaluronic acid; thereby producing stable cartilage locally at the site.

In some embodiments, the cartilage is stable for more than 5 weeks after administering the construct composed of naïve bone morrow stromal cells and fibrin microbeads with covalently attached hyaluronic acid. In embodiments, the cartilage is stable for more than 8 weeks after administering the construct.

In additional embodiments, the cartilage is hyaline-like cartilage. In further embodiments, the cartilage expresses type II collagen, aggrecan, or both. In other embodiments, the cartilage does not express type X collagen at 28 weeks after administering the bone marrow stromal cells. In yet other embodiments, naïve bone marrow stromal cells express one or more of CD29, CD73, CD90, CD140b, and CD146.

In some embodiments, administration is via injection to a site of interest, such as the site of an injury or degenerative condition. In additional embodiments, the injection is intra-articular or via a trans-osseous approach. In further embodiments, administration is via minimally invasive surgical procedure. In specific non-limiting embodiments, administration is to a knee, shoulder, wrist or hip.

In further embodiments, administration repairs a subchondral bone injury. The subchondral bone injury can be any type of fracture. Specific non-limiting examples include a microtrauma, microfracture, or subchondral fracture that is present with a proportion of cartilage injury.

In some embodiments, the subject is at risk of developing, or has, osteoarthritis, osteochondritis dissecans, osteochondrodysplasias, or cartilage injury. In embodiments, the subject has bone damage.

In additional embodiments, the method further includes producing the fibrin microbeads by mixing fibrinogen with thrombin and immediately adding in oil preheated to a temperature of 60-80° C., thereby producing a suspension of fibrin gel droplets in the oil; and mixing the suspension for 4-10 hours (hrs), thereby producing the fibrin microbeads. In embodiments, the fibrin microbeads do not comprise methacrylic anhydride. In embodiments, the fibrin microbeads comprise 70% fibrin or more. In embodiments, the fibrin microbeads comprise a density of greater than 1.15 g/mL. In embodiments, the fibrin microbeads comprise a density of 1.25-1.35 g/mL. In embodiments, the fibrin microbeads have a mean diameter of 60-250 μm.

In further embodiments, the hyaluronic acid is crosslinked to the fibrin microbeads by 1-ethyl-3-(3-(dimethylamino)propyl) carbodiimide (EDC), divinyl sulfone (DVS), glutaraldehyde (GTA), and/or poly(ethylene glycol) diglycidyl ether (EX 810). In an embodiment, the hyaluronic acid is high molecular weight hyaluronic acid. In embodiments, the hyaluronic acid has an estimated size range of about 50,000-200,000 Da.

In yet other embodiments, the subject is human. In further embodiments, the naïve bone marrow stromal cells are autologous, allogeneic, or heterologous. In more embodiments, the naïve bone marrow stromal cells are human bone marrow stromal cells. In another embodiment, the mixtures of autologous BMSCs with HyA-FMB are injected into cartilage lesions in animals, such as wounded horses.

In some embodiments, the method further includes administering an anti-inflammatory agent to the subject, such as, but not limited to, a non-steroidal anti-inflammatory agent.

Also disclosed herein is a composition including naïve bone marrow stromal cells attached to fibrin microbeads with crosslinked hyaluronic acid for use in promoting cartilage growth and/or repair in a subject, such as a human subject that has an injury or degenerative condition of the cartilage.

The foregoing and other objects, features, and advantages of the invention will become more apparent from the following detailed description, which proceeds with reference to the accompanying figures.

BRIEF DESCRIPTION OF THE DRAWINGS

FIGS. 1A-1H: (FIG. 1A) Scheme of subcutaneous transplantation of naïve hBMSCs with fibrin microbeads (FMBs), FMBs with covalently bound hyaluronic acid (HyA-FMBs), and FMBs or HyA-FMBs without cells (empty) into immunocompromised mice. (FIG. 1B) Details for Group 1 mice. Naïve hBMSCs attached to the FMBs or HyA-FMBs were delivered subcutaneously through a 0.5-cm-long skin incision, using separate 1-ml tuberculin syringes without needles. To reduce the dead volume, the narrow tip of the syringe was cut away such that the plunger could push the construct (having the consistency of wet snow) all the way through the syringe and under the skin. In this way, the transplants were placed 0.5-1 cm away from the incisions. Incisions were closed with a single clip. All transplants were recovered. More cartilage was formed by hBMSC/HyA-FMBs than by hBMSCs/FMBs ($3.0 \pm 0.7$ vs. $1.2 \pm 1.1$, respectively, *p=0.0317). Bone was also formed in both types of transplants, but with no statistical difference (ns). Macroscopic views of cartilage formed by hBMSC/FMB transplants in (FIG. 1C), and by hBMSC/HyA-FMB transplants in (FIG. 1D), which were larger in size. Staining of hBMSC/FMB transplants with H&E (FIG. 1E) revealed strong basophilic staining of the extracellular matrix in areas with cartilage morphology. Bone, sometimes supporting hematopoiesis, and fibrous tissue were found at the periphery of the transplants. Cartilage-like areas were stained purple with toluidine blue (TB) (FIG. 1F). Cartilaginous areas were more extensive in hBMSC/HyA-FMB transplants as demonstrated by H&E staining (FIG. 1G), and TB staining (FIG. 1H). Residual FMBs were found in both types of transplants. a=adipocytes; b=bone; c=cartilage; f=residual FMBs; ft=fibrous tissue; hp=hematopoiesis; H&E=hematoxylin and eosin; NSG=immunocompromised mouse strain; TB=toluidine blue (metachromatic staining of cartilage matrix).

FIG. 2: Details for Group 2 mice. Subcutaneous transplants of naïve hBMSCs were generated with FMBs, with and without covalently bound hyaluronic acid (HyA-FMBs). Some transplants were generated without naïve hBMSCs (empty), into immunocompromised mice (NSG). Naïve hBMSCs attached to the HyA-FMB were transplanted subcutaneously via open surgery. After making a central dorsal incision of ~2 cm in the back of a 8-15-wk-old female mouse, each transplant was placed, using a spatula, into a subcutaneous pocket, with up to 4 transplants per animal; an effort was made to place each transplant as far from the incision as possible. The incision was closed with three or four 9-mm steel wound clips (Roboz Surgical Instrument Co., Inc., Rockville, Md.).

FIGS. 5A-5H: Subcutaneous transplants of FMBs, with covalently bound hyaluronic acid (HyA-FMBs) with naïve hBMSCs into immunocompromised mice (NSG and SHC) at 28 wks. (FIG. 5A and FIG. 5C) The white, glossy appearance of the transplants persisted (insets), and vast fields of cartilage were found by H&E staining of transplants retrieved from both NSG and SHC mice. (FIG. 5B and FIG. 5D) The cartilage matrix stained intensely purple with TB, and small islands of bone were noted on the periphery of transplants in both strains of mice (insets). (FIG. 5E) Cartilage matrix stained intensely positive for Type II collagen in NSG transplants. Similar results were found in SHC transplants. On the other hand, no staining of Type X collagen was noted in SHC transplants. Similar results were observed in NSG transplants. (FIG. 5F) Cartilage was found to be of human origin based on staining with a human-specific anti-mitochondrial antibody (FIG. 5G). Specificity of the immunohistochemistry for Type II collagen, Type X collagen, and human mitochondria was demonstrated by the lack of staining with an isotype control (all three antibodies were of the same isotype) (FIG. 5H).

FIGS. 6A-6D: 0.5 mm Microdrilling of Mouse Trochlea (FIG. 6A); High resolution radiograph of 0.5 mm defect with Barium Sulfate Fill (FIG. 6B); 0.5 mm trochlear defect under 5× magnification (FIG. 6C); trochlear defect after filling with collagen scaffold (FIG. 6D).

DETAILED DESCRIPTION

Overview

Figure 1A:
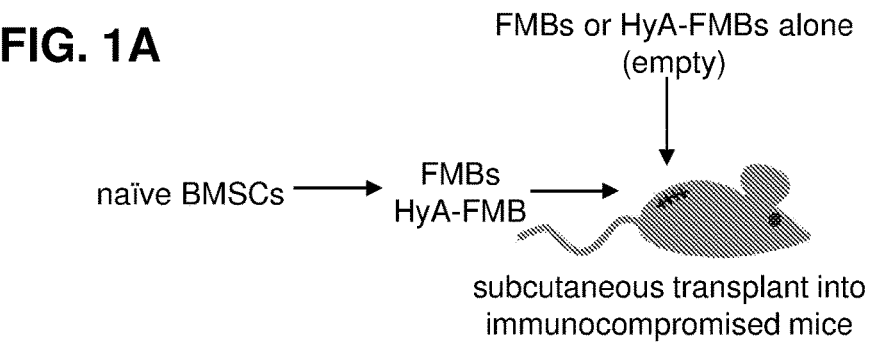

It is disclosed herein that stable cartilage is formed when naïve BMSCs were combined with fibrin microbeads (FMBs) crosslinked to hyaluronic acid (HyA-FMBs), and then transplanted into immunocompromised mice. In embodiments, naïve hBMSCs attached to HyA-FMBs can form permanent, hyaline-type human cartilage that does not undergo hypertrophy or degradation, even in the hostile, so-called non-permissive subcutaneous environment in immunocompromised mice Methods of the present disclosure use fibrin microbeads crosslinked to hyaluronic acid (HyA-FMBs) as a scaffold that supports cartilage formation by naïve (undifferentiated) bone marrow stromal cells (BMSCs). The methods of the present disclosure can be used in the promotion of growth or repair of stable hyaline-like human cartilage in vivo by naïve BMSCs in combination with FMBs modified with hyaluronic acid (HyA-FMBs), serving as a slowly degrading scaffold. The methods of the present disclosure demonstrate formation of stable cartilage in vivo by using the combination of HyA-FMBs with naïve BMSCs, which provides new possibilities for the restoration of damaged articular cartilage in regenerative medicine, and is applicable to any human disease wherein regeneration of cartilage in vivo is beneficial.

In embodiments, naïve BMSCs (e.g., allogeneic or autologous BMSCs) are attached to (e.g., mixed with) HyA-FMBs. The BMSCs attached to HyA-FMBs are locally administered to a subject in need or wounded animal. In embodiments, a subject in need thereof is at risk of developing, or has, osteoarthritis, osteochondritis dissecans, osteochondrodysplasias, or a cartilage injury. A subject in need thereof can additionally have bone damage; e.g., from osteoarthritis or accidental injury. In other embodiments the HyA-FMB are injected to cartilage damages in animals such as wounded horses.

Administration of the HyA-FMBs is local, at a site with damaged cartilage. The site can be a joint; e.g., knee, hip, wrist, shoulder, elbow, ankle, or other. In embodiments, administration to the site is via injection or minimally invasive surgery.

Following administration of the HyA-FMBs there is cartilage growth or repair, and the cartilage is stable in vivo. In embodiments, cartilage is stable for more than about 5 weeks, 6 weeks, 7 weeks, 8 weeks, 9 weeks, 10 weeks, 3 months, 6 months, 9 months, one year or more, after in vivo administration of BMSCs mixed with HyA-FMBs.

In embodiments, an in vivo transplantation model system can be developed for the study of pathological mechanisms of human genetic and acquired diseases of cartilage.

Terms

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting.

In order to facilitate review of the various embodiments of the disclosure, the following explanations of specific terms are provided:

1-ethyl-3-(3-(dimethylamino) propyl) carbodiimide (EDC) is a water-soluble carbodiimide crosslinker that activates carboxyl groups for spontaneous reaction with primary amines. The structure of EDC is shown below:

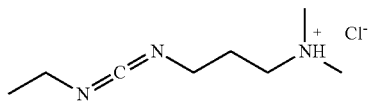

Administration is to give a subject a therapeutic intervention, such as a therapeutic composition, procedure, or protocol (e.g., for a subject with a cartilage disease or injury). Exemplary routes of administration for a therapeutic composition include, but are not limited to injection (such as intra-articular injection) or minimally invasive surgical procedure.

Aggrecan, also referred to as cartilage-specific proteoglycan core protein. Aggrecan can be identified by a specific antibody as a marker for the presence of cartilage. UniProt Databank identified for human aggrecan is 4MD4. Aggrecan sequences are publicly available. For example, GENBANK® Accession Nos. NM_001135.3, NM_022190.1, NM_007424.2 disclose exemplary human, rat, and mouse aggrecan nucleotide sequences, respectively, and GENBANK® Accession Nos. NP_001126.3, NP_071526.1, NP_031450.2 disclose exemplary human, rat, and mouse aggrecan protein sequences, respectively. These GENBANK® entries are incorporated by reference as available on May 24, 2017. One of ordinary skill in the art can identify additional aggrecan nucleic acid and protein sequences, including isoform and transcript variants, peptide fragments, and peptides containing phosphorylation sites.

Attached indicates entities that are joined, conjugated, or combined, and includes covalent, ionic, polar or hydrogen bonds as well as the combination of materials, particles or molecules mixed together; e.g., fibrin microbeads mixed with hyaluronic acid.

Bone defect: Includes any disease, defect, or disorder which affects bone strength, function, and/or integrity, such as those resulting from injury, or a defect brought about during the course of surgery, infection, malignancy, or developmental malformation. Examples of bone defects include, but are not limited to, fractures (such as a microtrauma, a microfracture, or a subchondral fracture), dental or facial defects (such as cleft palate or facial, skull, or dental injuries or malformations). Other examples of bone defects include damage to bones resulting from diseases of bone fragility, such as osteoporosis, and malignancies and/or cancers of the bone such as a sarcoma, such as osteosarcoma.

Bone Healing and Fracture Healing: Bone heals (fuses) in a unique way compared with other connective tissues. Rather than develop scar tissue, it has the innate ability to regenerate itself completely. Without being bound by theory, it is generally believed that the fracture healing sequence involves five discrete stages of healing. This includes an initial stage in which a hematoma is formed and inflammation occurs; a subsequent stage in which cartilage begins to form and angiogenesis proceeds, and then three successive stages of cartilage calcification, cartilage resorption and bone deposition, and ultimately a more chronic stage of bone remodeling. Generally, committed osteoprogenitor cells and uncommitted, undifferentiated mesenchymal cells contribute to the process of fracture healing. Generally, two weeks after fracture, cell proliferation declines and hypertrophic chondrocytes become the dominant cell type in the chondroid callus, and undergo further matrix mineralization, followed by infiltration of bone-forming cells. The resulting endochondral bone is formed adjacent to the fracture site.

Bone Marrow Stromal Cells (BMSCs), also referred to as Bone Marrow-Derived Mesenchymal "Stem Cells" or naïve BMSCs, are a small fraction of cells in bone marrow that are stem cell-like precursors for skeletal lineage including osteocytes, chondrocytes, and adipocytes and hematopoiesis supportive stroma. Bone marrow stromal cells have been studied extensively (Castro-Malaspina et al., 1980, Blood 56:289-30125; Piersma et al., 1985, Exp. Hematol 13:237-243; Simmons et al., 1991, Blood 78:55-62; Beresford et al., 1992, J. Cell. Sci. 102:341-351; Liesveld et al., 1989, Blood 73:1794-1800; Liesveld et al., Exp. Hematol 19:63-70; Bennett et al., 1991, J. Cell. Sci. 99:131-139). Bone marrow stromal cells can be derived from any animal. In some embodiments, stromal cells are derived from primates, preferably humans. Human BMSCs are also referred to as hBMSCs. Naïve BMSCs refers to BMSCs that have not received a treatment differentiate them, particularly to induce the BMSCs to form cartilage-forming cells, bone-forming cells, or an andipocyte-forming cells, see Satoma et al., J Cell Biochem. 2000 Jun. 6; 78(3):391-403, incorporated herein by reference. Naïve BMSCs are grown in standard culture conditions that do not enhance one cell phenotype over another (e.g. to promote differentiation into a cartilage-forming cell, a bone-forming cell, or an adipocyte-forming cell.)

BMSCs can be identified by expression of one or more of CD29, CD73, CD90, CD140b, and CD146, for example by using fluorescence activated cell sorting (FACS).

In some embodiments, BMSCs used in the methods of the present disclosure are autologous. In other embodiments, BMSCs used in the methods of the present disclosure are allogeneic, as they are from a different animal of the same species. In embodiments, BMSCs are naïve BMSCs.

Cartilage is a smooth, elastic tissue covering and protecting the ends of bones (e.g., at joints). Cartilage is composed of chondrocytes that produce a large amount of collagenous extracellular matrix, and is rich in proteoglycan and elastin fibers. Hyaline cartilage, also referred to as hyaline-like cartilage, is a translucent or white cartilage containing no nerves or blood vessels. The presence of cartilage can be determined by the expression of protein, collagen Type II, or aggrecan. The expression of the protein, collagen Type X, indicates hypertrophic cartilage, destined to be degraded. In vivo, cartilage has limited repair capabilities. The methods of the present disclosure produce new cartilage that persists in its cartilage state in vivo without vascularization or ossification. In embodiments, the cartilage is stable for more than about 5 weeks, 6 weeks, 7 weeks, 8 weeks, 9 weeks, 10 weeks, 3 months, 6 months, 9 months, one year or more, after in vivo administration of naïve bone morrow stromal cells with fibrin microbeads with bound hyaluronic acid. Cartilage is radiolucent, however, clinically physicians can measure the distance between the boney epiphyses (joint space) as a surrogate to measure cartilage thickness.

Cartilage Injury is any injury or damage to the cartilage tissue. Cartilage injuries include tears, rips and ruptures. Cartilage injury typically occurs in the joints; e.g., knee, hip, wrist, elbow, shoulder, ankle, etc. Examples of cartilage injuries include meniscal tears, labral tears of the hip or shoulder, talar dome lesions, and others. Cartilage injuries can occur due to accident, athletic injury, or others.

CD29, also referred to as integrin beta-1, is a cell surface protein useful in the identification of BMSCs. CD29 is encoded by the ITGB 1 gene. The UniProt identifier for human CD29 is P05556. CD29 sequences are publicly available. For example, GENBANK® Accession Nos. NM_002211.3, NM_017022.2, NM_010578.2 disclose exemplary human, rat, and mouse CD29 nucleotide sequences, respectively, and GENBANK® Accession Nos. NP_596867.1, NP_058718.2, NP_034708.1 disclose exemplary human, rat, and mouse CD29 protein sequences, respectively. These GENBANK® entries are incorporated by reference as available on May 24, 2017. One of ordinary skill in the art can identify additional CD29 nucleic acid and protein sequences, including isoform and transcript variants, peptide fragments, and peptides containing phosphorylation sites.

CD73, also referred to as ecto-5'-nucleotidase, is a cell surface protein useful in the identification of BMSCs. CD73 is encoded by the NT5E gene. The UniProt identifier for human CD73 is P21589. CD73 sequences are publicly available. For example, GENBANK® Accession Nos. NM_002526.3, NM_021576.2, NM_011851.4 disclose exemplary human, rat, and mouse CD73 nucleotide sequences, respectively, and GENBANK® Accession Nos. NP_001191742.1, NP_067587.2, NP_035981.1 disclose exemplary human, rat, and mouse CD73 protein sequences, respectively. These GENBANK® entries are incorporated by reference as available on May 24, 2017. One of ordinary skill in the art can identify additional CD73 nucleic acid and protein sequences, including isoform and transcript variants, peptide fragments, and peptides containing phosphorylation sites.

CD90, also referred to as Thy-1, is a cell surface protein useful in the identification of BMSCs. CD90 is encoded by the THY1 gene. The UniProt identifier for human CD90 is P04216. CD90 sequences are publicly available. For example, GENBANK® Accession Nos. NM_006288.4, NM_012673.2, NM_009382.3 disclose exemplary human, rat, and mouse CD90 nucleotide sequences, respectively, and GENBANK® Accession Nos. NP_001298091.1, NP_033408.1, NP_036805.1 disclose exemplary human, rat, and mouse CD90 protein sequences, respectively. These GENBANK® entries are incorporated by reference as available on May 24, 2017. One of ordinary skill in the art can identify additional CD90 nucleic acid and protein sequences, including isoform and transcript variants, peptide fragments, and peptides containing phosphorylation sites.

CD140b, also referred to as Beta-type platelet-derived growth factor receptor, is a cell surface protein useful in the identification of BMSCs. CD140b is encoded by the PDGFRB gene. The UniProt identifier for human CD140b is P09619. CD140b sequences are publicly available. For example, GENBANK® Accession Nos. NM_002609.3, NM_031525.1, NM_001146268.1 disclose exemplary human, rat, and mouse CD140b nucleotide sequences, respectively, and GENBANK® Accession Nos. NP_002600.1, NP_113713.1, NP_001139740.1 disclose exemplary human, rat, and mouse CD140b protein sequences, respectively. These GENBANK® entries are incorporated by reference as available on May 24, 2017. One of ordinary skill in the art can identify additional CD140b nucleic acid and protein sequences, including isoform and transcript variants, peptide fragments, and peptides containing phosphorylation sites.

CD146, also referred to as melanoma cell adhesion molecule (MCAM) or cell surface glycoprotein MUC18, is a cell surface protein useful in the identification of BMSCs. CD146 is encoded by the MCAM gene. The UniProt identifier for human CD146 is P43121. CD146 sequences are publicly available. For example, GENBANK® Accession Nos. NM_006500.2, NM_023983.3, NM_023061.2 disclose exemplary human, rat, and mouse CD146 nucleotide sequences, respectively, and GENBANK® Accession Nos.

NP_006491.2, NP_076473.2, NP_075548.2 disclose exemplary human, rat, and mouse CD146 protein sequences, respectively. These GENBANK® entries are incorporated by reference as available on May 24, 2017. One of ordinary skill in the art can identify additional CD146 nucleic acid and protein sequences, including isoform and transcript variants, peptide fragments, and peptides containing phosphorylation sites.

Collagen is the main structural protein in connective tissues of animals. Collagen may vary in its degree in formation of various tissues, for example, bone, tendon, and cartilage. There are several types of collagen which are present in varying degrees in different tissues. Collagen Types I-V are most common. Collagen Type II is the main collagenous component of cartilage.

Collagen type II is encoded by the COL2A1 gene. The UniProt identifier for human Collagen type II is P02458. Collagen type II sequences are publicly available. For example, GENBANK® Accession Nos. NM_001844.4, NM_012929.1, NM_031163.3 disclose exemplary human, rat, and mouse Collagen type II nucleotide sequences, respectively, and GENBANK® Accession Nos. NP_001835.3, NP_001835.3, NP_112440.2 disclose exemplary human, rat, and mouse Collagen type II protein sequences, respectively. These GENBANK® entries are incorporated by reference as available on May 24, 2017. One of ordinary skill in the art can identify additional Collagen Type II nucleic acid and protein sequences, including isoform and transcript variants, peptide fragments, and peptides containing phosphorylation sites.

Collagen Type X is encoded by the COL10A1 gene. The UniProt identifier for human Collagen type X is Q03692. Collagen type X sequences are publicly available. For example, GENBANK® Accession Nos. NM_000493.3, XM_001053056.7, NM_009925.4 disclose exemplary human, rat, and mouse Collagen type X nucleotide sequences, respectively, and GENBANK® Accession Nos. NP_000484.2, XP_001053056.5, NP_034055.1 disclose exemplary human, rat, and mouse Collagen type X protein sequences, respectively. These GENBANK® entries are incorporated by reference as available on May 24, 2017. One of ordinary skill in the art can identify additional Collagen Type X nucleic acid and protein sequences, including isoform and transcript variants, peptide fragments, and peptides containing phosphorylation sites.

Crosslinking, also referred to as bioconjugation, is the process of covalently joining two or more molecules. Crosslinking reagents, or crosslinkers, contain two or more reactive ends capable of forming a covalent bond with a molecule of interest. Many chemical crosslinkers are available. Crosslinkers include, for example, 1-ethyl-3-(3-(dimethylamino) propyl) carbodiimide (EDC), or other cross-linker which can attach the HyA covalently to fibrin matrix without covalently with clearance of its residues after the reaction such as divinyl sulfone (DVS), glutaraldehyde (GTA), and/or poly(ethylene glycol) diglycidyl ether (EX 810).

Fibrin is a fibrous, non-globular protein, which is the proteolytic product of fibrinogen. The UniProt identifier for human fibrinogen is P02671. Fibrinogen sequences are publicly available. For example, GENBANK® Accession Nos. NM_021871.3, NM_001008724.1, NM_001111048.2 disclose exemplary human, rat, and mouse fibrinogen nucleotide sequences, respectively, and GENBANK® Accession Nos. NP_068657.1, NP_001008724.1, NP_001104518.1 disclose exemplary human, rat, and mouse fibrinogen protein sequences, respectively. These GENBANK® entries are incorporated by reference as available on May 24, 2017. One of ordinary skill in the art can identify additional fibrinogen nucleic acid and protein sequences, including isoform and transcript variants, peptide fragments, and peptides containing phosphorylation sites.

Fibrin Microbeads (FMBs) are microparticles primarily composed of fibrin. Fibrin microbeads and methods of making the same are included in U.S. Pat. Nos. 6,552,172; 6,503,731; and 6,150,505; incorporated by reference herein in their entireties.

Fibrin microbeads can be produced from dense fibrin gels, which are vigorously mixed in heated oil to temperature of 60-85° C. to form a suspension. This suspension is further mixed vigorously in the oil for 4-10 hrs to form the dense dehydrated fibrin microbeads. The microbeads can be further collected washed and dried to yield the basic fibrin microbeads structure. The microbeads can be further condensed into the shape of separate beads by dehydrothermal crosslinking. Fibrin microbeads can have a density of greater than greater than 1.15 g/mL, for example from about 1.1-1.4 g/mL, 1.2-1.4 g/mL, or 1.25-1.35 g/mL. In embodiments, fibrin microbeads contain 70% or more fibrin. The resultant solid fibrin microbeads can then be coated with HA.

Fracture: A medical condition in which a bone is cracked or broken; a break in the continuity of a bone. Fractures may be classified as closed or open. A closed fracture is one in which the skin is intact; an open (or compound) fracture is one in which the bone is in contact with the air (such as piercing the skin or due to severe tissue injury). Fractures are also classified as simple or multi-fragmentary. A simple fracture occurs along only one line (such as splitting a bone into two pieces), while a multi-fragmentary fracture splits a bone into multiple pieces (such as three or more pieces). Other types of fracture include complete, incomplete, linear, transverse, oblique, compression, spiral, comminuted, and compacted fractures. Additional fractures include a critical defect (such as when part of a bone is lost or removed) and a non-union fracture (such as when the ends of the fracture are not in contact with each other). "Microfracture" refers to a pattern of bony injury resulting from trauma that does not cause gross, clinically apparent fracturing. This damage results in disruptions in mineral and protein compartments of bone, leading to reduced structural integrity, and resulting in hemorrhage, edema, and infarction, often characterized clinically by increased bone or marrow T2 MRI signal. Microfacture is commonly observed in joint injuries involving abnormal loading of the cartilage and subchondral bone (e.g., anterior cruciate ligament tears, meniscal tears, and patella dislocations) and often accompanies cartilage or ligament injury. This phenomenon of microscopic bony injury and the subsequent molecular processes are involved in post-traumatic osteoarthritis.

Growth refers to an increase in the amount of a tissue, for example cartilage. Growth can be assessed by expansion in size, weight, or progression of tissue development.

Hyaluronic Acid (HyA), also referred to as hyaluronan or HA, is an anionic, nonsulfated glycosaminoglycan distributed widely throughout connective, epithelial, and neural tissues. HyA has a monomeric structure as shown below:

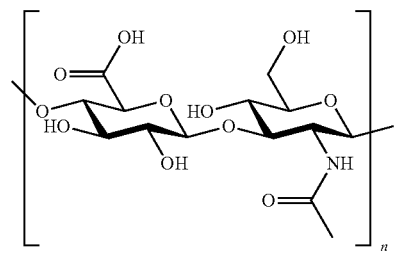

HyA can be high molecular weight hyaluronic acid, for example with an estimated size range of about 50,000-200,000 Da.

Intra-articular, or intraarticular, refers to within a joint; e.g., an intra-articular procedure or injection. In embodiments, an intra-articular procedure is within a hip, wrist, elbow, knee, shoulder, or ankle joint. In embodiments, intra-articular injection is ultra sound guided. Intra-articular can also refer to a minimally invasive surgical procedure; e.g., intra-articular laparoscopic surgery.

Osteoarthritis is a type of joint disease resultant from the breakdown of cartilage and bone within the joints. Osteoarthritis causes joint pain and stiffness, swelling and decreased range of motion. The cartilage covering bones (articular cartilage—a subset of hyaline cartilage) is thinned, eventually completely wearing away, resulting in a "bone against bone" within the joint, leading to reduced motion, and pain.

Repair refers to the regrowth of tissue, for example, the repair of torn or degraded cartilage following injury or disease. Repair does not necessarily indicate full restoration to a pre-injury, or pre-disease state. Repair can include partial repair, for example about 10%, 20%, 30%, 40%, 50%, 60%, 70%, 80%, 90%, 95%, 99%, or more regrowth in injured tissue. Repair can be measured as a percentage extension in length, height, width, diameter, or weight. Repair can further be measured as an increase in joint mobility, or subjectively, as in increase in joint comfort.

Subject: Includes both human and veterinary subjects, such as humans, non-human primates, pigs, sheep, cows, rodents, birds, and the like, which can be the recipient of the disclosed methods. An "animal" is a living, multi-cellular vertebrate organisms, a category that includes, for example, mammals and birds (e.g., chickens). The term mammal includes both human and non-human mammals. In two non-limiting examples, a subject is a human subject or a murine subject.

Unless otherwise explained, all technical and scientific terms used herein have the same meaning as commonly understood by one of ordinary skill in the art to which a disclosed invention belongs. The singular terms "a," "an," and "the" include plural referents unless context clearly indicates otherwise. Similarly, the word "or" is intended to include "and" unless the context clearly indicates otherwise. "Comprising" means "including." Hence "comprising A or B" means "including A" or "including B" or "including both A and B."

Suitable methods and materials for the practice and/or testing of embodiments of the disclosure are described below. Such methods and materials are illustrative only and are not intended to be limiting. Other methods and materials similar or equivalent to those described herein can be used. For example, conventional methods well known in the art to which the disclosure pertains are described in various general and more specific references, including, for example, Sambrook et al., Molecular Cloning: A Laboratory Manual, 2nd ed., Cold Spring Harbor Laboratory Press, 1989; Sambrook et al., Molecular Cloning: A Laboratory Manual, 3d ed., Cold Spring Harbor Press, 2001; Ausubel et al., Current Protocols in Molecular Biology, Greene Publishing Associates, 1992 (and Supplements to 2000); Ausubel et al., Short Protocols in Molecular Biology: A Compendium of Methods from Current Protocols in Molecular Biology, 4th ed., Wiley & Sons, 1999; Harlow and Lane, Antibodies: A Laboratory Manual, Cold Spring Harbor Laboratory Press, 1990; and Harlow and Lane, Using Antibodies: A Laboratory Manual, Cold Spring Harbor Laboratory Press, 1999.

All publications, patent applications, patents, and other references mentioned herein are incorporated by reference in their entirety for all purposes. All sequences associated with the GENBANK® Accession numbers mentioned herein are incorporated by reference in their entirety as were present on May 24, 2017, to the extent permissible by applicable rules and/or law.

Naïve Bone Marrow Stromal Cells

Bone marrow stromal cells (BMSCs) can be produced by a number of methods. In embodiments, BMSCs used in the methods of the present disclosure are autologous. For example, bone marrow can be harvested from a subject in need of cartilage growth or repair, for example by bone marrow aspiration. Thus, the BMSCs can be autologous. However, BMSCs can be allogeneic, as they can be harvested from a different subject of the same species. In some embodiments, the BMSCs are human. However, BMSCs can be obtained from other subjects, including non-human primate and veterinary subjects.

In embodiments, BMSCs used in the methods of the present disclosure are allogeneic. For example, donor tissue, for example from a cadaver or amputated bone, can be used to establish BMSC cultures. In embodiments, human donor tissue may be used for the development of BMSC cultures for administration to a veterinary subject; e.g., a mouse. In embodiments, human donor tissue is used for developing BMSC cultures for administration to another human subject.

Bone marrow can readily be obtained by aspiration from a living or cadaveric subject. To establish primary BMSCs, bone marrow-derived nucleated cells can be plated and cultured. For example, $1\text{-}10 \times 10^7$ cells, $1\text{-}10 \times 10^6$ cells, or $1.5\text{-}5 \times 10^6$ cells can be cultured in standard tissue culture conditions, such as, but not limited to, in filter cap tissue flasks at a density of, for example, $1\text{-}10 \times 10^4$ cells, $1\text{-}8 \times 10^4$ cells, or $2\text{-}6.7 \times 10^4$ cells/cm$^2$.

The cells are cultured generally at about 37° C. in about 5% $CO_2$. In some non-limiting examples, culture medium can be αMEM, 2 mM glutamine, 100 U/ml penicillin, 100 μg/ml streptomycin sulfate (all Invitrogen), 20% non-heat-inactivated fetal bovine serum (FBS) of a pre-selected lot (Kuznetsov et al., Transplantation. 2000; 70(12): 1780-7) (Atlanta Biologicals, Inc., Lawrenceville, Ga.), dexamethasone (Sigma, St. Louis, Mo.) at $1 \times 10^{-8}$ M, and L-ascorbic acid phosphate magnesium salt n-hydrate (Wako, Osaka, Japan) at $10^{-4}$ M. To obtain the cells from the cultures, they can be washed and the adherent cells detached from the tissue culture surface. In one non-limiting example, cultures can be washed, for example with Hanks' Balanced Salt Solution, and detached from culture flasks, for example with 0.05% Trypsin-EDTA and passaged. However, these should not be construed to be limiting. For example, phosphate buffered saline can also be used as a washing solution. BMSCs for use in cartilage growth or repair may be passed, for example 1 time, 2 times, 3 times, 4 times, 5 times, or more prior to mixing with and attachment to fibrin microbeads for administration. Naïve BMSCs of the present disclosure are not treated for pre-differentiation (e.g. differentiation into a cartilage-forming cell, a bone-forming cell, or an adipocyte-forming cell).

In some embodiments, BMSCs can be identified by expression of one or more of CD29, CD73, CD90, CD140b, and CD146, for example by using fluorescence activated cell sorting (FACS). In other embodiments, BMSCs are segregated from mixed cell cultures using FACS to identify one or more of the above cell markers.

BMSCs can be mixed with and/or attached to fibrin microbeads for administration. In embodiments, HyA-FMB can be washed and resuspended, for example in culture media. For mixing, and attachment or adhesion to, the FMBs in suspension can be combined with a suspension of HyA-FMBs, for example by slow rotation, for 30 minutes, 40 minutes, 60 minutes, 70 minutes, 80 minutes, 90 minutes, 120 minutes, or more. In embodiments, mixing of FMBs with BMSCs is at 37° C.

In some embodiments, FMBs (see below) are sterilized, and washed. The BMSCs are then added to the FMBs in a tissue culture medium, such as at a temperature of about 37° C. and allowed to adhere to the FMBs, such as for 30 minutes to 2 hours, or for 1 hour to 2 hours. Suitable incubation times include, but are not limited to, about 30, about 45, about 60, about 75, about 90, about 105, or 120 minutes.

Fibrin Microbeads

Fibrin microbeads are microparticles primarily composed of fibrin. Fibrin is a proteolytic product of fibrinogen, a glycoprotein. Fibrin microbeads and methods of making the same are included in U.S. Pat. Nos. 6,552,172; 6,503,731; and 6,150,505; incorporated by reference herein in their entireties.

In some embodiments, fibrin microbeads have a density of greater than greater than 1.15 g/mL, for example from about 1.1 to about 1.4 g/mL, about 1.2 to about 1.4 g/mL, or about 1.25 to about 1.35 g/mL. In further embodiments, fibrin microbeads contain 70% or more fibrin, for example 71% fibrin, 72% fibrin, 73% fibrin, 74% fibrin, 75% fibrin, or more. Without being bound by theory, the dense structure and mechanical stability of fibrin microbeads resists vascularization and allows for stable cartilage formation from bone marrow stromal cells in vivo. In embodiments, microbeads have a diameter of about 40-300 µm, or about 60-250 µm.

In some embodiments, an aqueous solution comprising fibrinogen, thrombin and factor XIII is prepared, such as by combining fibrinogen containing endogenous factor XIII with thrombin, by combining cryoprecipitate containing endogenous fibrinogen and endogenous factor XIII with thrombin, or by combining fibrinogen, factor XIII and thrombin individually into an aqueous solution. Alternatively, sources containing blood plasma fractionation products of procedures which enriches their fibrinogen concentration, such as cryo-precipitate ("paste 1") with fibrinogen concentration above 10 mg/ml, including crude could also be used as the source of the fibrinogen. Equivalent fibrinogen activating proteases such as snake venom proteases (e.g., reptilase) can be used as an alternative to thrombin. In some embodiments, the ratio of fibrinogen:thrombin:factor XIII in the aqueous solution is about 5 to about 100 mg/mL, about 1 to about 100 U/mL, about 1 to about 50 U/mL, about 20 to about 40 mg/mL, about 5 to about 10 U/mL, or about 2 to about 20 U/mL. In addition, the aqueous solution also can contain co precipitating proteins such as fibronectin and other blood-derived proteins that may be present in the rich fibrinogen solution and cryoprecipitate starting materials.

The aqueous solution with fibrinogen and activating protease, such as thrombin, immediately after their mixing is introduced into a very fast mixed and stirred oil heated to a temperature in the range of 60 to about 85° C. to form an emulsion with continuous fast stirring. Any hydrophobic organic solvent such as isooctane also may be included in the oil. The suspension is mixed in the oil for about 3 to about 10 hours, such as about 4 to about 10 hours. The mixing speed will depend upon the volume of the emulsion, and the desired size of the microbeads. For example, volumes of >400 mL oil and about 100 mL aqueous phase in a 1 L flask, an exemplary vigorous mixing speed is at least 300-500 rpm.

Fibrin microbeads can be isolated from the emulsion using procedures such as centrifugation, filtration, rinsing in different organic solvents and alcohols or a combination thereof. The isolated fibrin microbeads may can be washed with solvents, such as, but not limited to, hexane, acetone and/or ethanol and ether, and then air dried in ambient temperature moderately heated in atmospheric pressure or in vacuum heated or no heated condition. The microbeads may then be graded to the desired size using commercially available filters or sieves. Preferably, the fibrin microbeads of the present invention are graded to a diameter of about 80-250 microns, although larger or smaller fibrin microbeads may be utilized. In some embodiments, the microbeads can be further condensed by dehydrothermal crosslinking, either before or after grading them into fractions of the desired size. Not to be bound by theory, the long time stirring in heated oil results with full dehydration of the small hydrous fibrin gel initially containing hydrous droplets which dry slowly and eventually results in the spontaneous dehydrothermal non-reversible covalent crosslinking of the proteins by the long exposure of many hours to the ambient moderately high temperature.

In some non-limiting examples, fibrin microbeads can be produced from dense fibrin gels which are vigorously mixed in heated oil to temperature of 60-80° C. to form a suspension. This suspension is further mixed vigorously in the oil for 4-10 hours to form the dense dehydrated fibrin microbeads. The microbeads can be further collected washed and dried to yield the basic fibrin microbeads structure. The microbeads can be further condensed into the shape of separate beads by dehydrothermal crosslinking. Protocols are disclosed for example, in Gorodetsky et al., J Invest Dematol. 1999; 112(6):866-72 and Gorodetsky, Expert Opin Biol Ther. 2008; 8(12):1831-46, both incorporated herein by reference, in their entireties.

In other non-limiting examples, frozen plasma-derived fibrinogen-enriched solution was purified by sedimentation. A concentrated solution of about 40-80 mg/mL, about 50-70 mg/mL, or about 55-65 mg/mL of clotable, soluble protein was obtained. To form FMBs, the fibrinogen solution was mixed with thrombin/Ca+2 to reach a final concentration of about 0.5-10 U/mL, about 1-8 U/mL, or about 1-6 U/mL thrombin and about 2-6 mM $Ca^{2+}$, or about 4 mM $Ca^{+2}$. Upon initiation of coagulation, the mixture was immediately poured into a heat-stable oil; e.g., pure medium-chain-triglycerides oil (MCT, Edomim-Food Supplements, Israel) or any other similar oxidation resistant oil heated to reach a temperature of about 60-85° C., in a heavy-duty mixer attached to a temperature controlled heater. An emulsion with small, concentrated fibrin gel droplets floating as a suspension in the oil, was formed and stabilized within about 15 min-1 hour, about 20-50 min, or about 30-45 min. Following an additional about 4-10 hrs, about 5-9 hours, or about 6-8 hrs of continuous mixing at high speed, condensed, dehydrothermally stabilized FMBs are formed in the heated oil. The resulting solid FMBs are collected and thoroughly washed to remove oil residue by a series of rinses; e.g., initially with hexan, then with acetone, followed by final rinses in an ethanol gradient of 70%, 96% and 100%. Dried FMBs are mesh-sieved, and the size range between about 50-250 µm, about 80-200 µm, or about 105-180 µm are collected and stored at room temperature (RT) for further use. FMB can be stored for a period of greater than 5 years without notable detriment.

Fibrin microbeads can be coated with (e.g., crosslinked to) HyA. In embodiments, fibrin microbeads can be coated with HyA using a crosslinking agent, for example divinyl sulfone (DVS), glutaraldehyde (GTA), poly(ethylene glycol) diglycidyl ether (EX 810), and/or EDC. In embodiments, HyA can be mixed, for example by shaking, with a solution of fibrin microbeads, about 30 minutes to about 6 hours, such as for about 30 minutes, about 1 hour, about 2 hours, about 3 hours, about 4 hours, about 5 hours, or 6 hours in the presence of a cross-linking agent. Longer times intervals could also be used. Following mixing, the fibrin microbeads with crosslinked HyA can be isolated. In one embodiment, they are allowed to settle and the supernatant removed for rinsing in series of organic solvents and resuspension to rinse away the residual oil, drying in air or vacuum in ambient or moderate heating in up to ~70° C.

In one, non-limiting example, modification of FMBs with hyaluronic acid to generate HyA-FMBs is performed by a covalent reaction with the crosslinker, 1-ethyl-3-(3-(dimethylamino) propyl) carbodiimide (EDC). About 20-60 mg, about 30-50 mg, or about 40 mg EDC is added to about 400-900 mg, about 500-700 mg, or about 600 mg of FMBs soaked in water at RT and mixed thoroughly for about 10 min-1 hour, about 15 min-45 min, or about 30 min. High molecular weight HyA with an estimated molecular size range of ~50-200,000 Da (about 30-50 ml, or about 40 ml of 1 mg/ml solution) is added and the solution was mixed for additional about 1-4, about 1-3, or about 2 hrs in a shaker. The complexed HyA-FMB are rinsed residual non-crosslinked HyA solution and EDC removed. The rinsed HyA-coated FMBs are re-suspended.

Administration

Naïve BMSCs attached to HyA-FMBs are administered locally at a site in a subject wherein the formation of stable cartilage is desirable. The site may be intra-articular; e.g., at a joint, for example hip, knee, shoulder, ankle, wrist, elbow, etc. Routes of administration include injection or minimally invasive surgery. In embodiments, an injection is an ultrasound guided injection. Minimally invasive surgery, also referred to as laparoscopic surgery, bandaid surgery, or keyhole surgery is a surgical procedure meant to minimize tissue damage and ease recovery. Minimally invasive surgery can be robotic, or non-robotic (e.g., endoscopic). However, the surgery may not be minimally invasive. BMSCs attached to HyA-FMBs can be used at the time of a major surgery, such as during a joint surgery or replacement, or when a bone is set.

By way of example, one method of administration to the knee, hip and/or shoulder of an individual is by intra-articular injection. For administration to the knee, for example, the joint to be injected is washed with a betadine solution or other antiseptic. A solution of an anesthetic, such as about one percent lidocaine hydrochloride is injected into the skin and subcutaneous tissue. A 3-way stopcock/needle assembly is utilized to administer the compound via an 18-30 gauge needle. The BMSCs attached to HyA-FMBs are injected into the joint space using a standard lateral approach well known to those skilled in the art. The needle and needle tract are cleansed by flushing with 1% lidocaine hydrochloride through the 3-way stopcock assembly as the needle is withdrawn. The knee is then moved through a flexion-extension arc and then immobilized in full extension. The patient is then confined to bed for approximately 24 hours to minimize movement and minimize leakage of FMBs from the joint.

In embodiments, an individual administration can include about 5 mg, 10 mg, 15 mg, 20 mg, 30 mg, 40 mg, 50 mg, 60 mg, 70 mg, 80 mg, 90 mg, 100 mg, or more milligrams of suspended BMSCs mixed with HyA-FMBs. An individual administration can include at least $1\times10^4$, $1\times10^5$, $1\times10^6$, $1\times10^7$, $1\times10^8$ or more cells. Administration may be a single administration or multiple administrations, such as 2, 3, 4, 5, or more administrations. Multiple administrations may be separated by at least 1 day, 2 days, 3 days, 4 days, 5 days, 6 days, 1 week, 2 weeks, 1 month, 2 months, 3 months, 6 months, 1 year, or more. In embodiments, administration can be to one or more joints.

The disclosed compositions be administered in conjunction with, following, or prior to, treatment with anti-inflammatory agents; e.g., non-steroidal anti-inflammatories. Nonsteroidal anti-inflammatories include, but are not limited to, salicylates, propionic acid derivatives, acetic acid derivatives, enolic acid derivatives, anthranilic acid derivatives, selective COX-2 inhibitors, sulfonanilides. Common nonsteroidal anti-inflammatories include, for example, aspirin, ibuprofen and naproxen.

In particular examples, anti-arthritis agents can be used. In some embodiments, the anti-arthritis agent is a biological response modifier, such as KINERET® (anakinra), ENBREL® (etanercept), or REMICADE® (infliximab), a disease-modifying antirheumatic drug (DMARD), such as ARAVA® (leflunomide), a steroid, such as prednisone or cortisone, a nonsteroidal anti-inflammatory drug (NSAID), such as celecoxib, choline magnesium trisalicylate, diclofenac, diclofenac potassium, diclofenac XR, diflunisal, etodolac, etodolac ER, fenoprofen, flurbiprofen oral, ibuprofen, indomethacin, indomethacin SR, indomethacin suppositories, ketoprofen, ketoprofen ER, meclofenamate, meloxicam, nabumetone, naproxen, naproxen CR, naproxen ER, oxaprozin, piroxicam, rofecoxib, salsalate, sulindac, or tolmetin sodium, or another product, such as HYALGAN® (hyaluronan) or SYNVISC® (hylan G-F20).

Stable Cartilage

Methods of the present disclosure are useful in promoting cartilage growth and/or repair by producing stable cartilage. In embodiments, administration of BMSCs attached to HyA-FMBs can produce cartilage at and/or around the administration site. In embodiments, the cartilage is hyaline cartilage. In embodiments, the presence of cartilage can be determined by the expression of Collagen Type II, or aggrecan. In embodiment, the expression of collagen Type X indicates non-cartilaginous tissues. Cartilage is radiolucent, however, clinically physicians can measure the distance between the boney epiphyses (joint space) as a surrogate to measure cartilage.

Cartilage is sometimes the initial stage in the development of ossified tissue in vivo following BMSC transplantation (it goes on to hypertrophy before forming bone). Prior studies using pre-treated BMSCs (e.g. treated with cartilage inducing factors in vitro) that are then transplanted in vivo have failed to form stable cartilage in vivo. The methods of the present disclosure utilize naïve BMSCs that have not been pre-treated to induce differentiation to cartilage-forming cells prior to their introduction in vivo. Cartilage produced by methods of the present disclosure is not a cartilage that goes on to hypertrophy before the development of bone, or other ossified tissue, but persists in a cartilage state. In some embodiments, this stable cartilage persists in vivo for a period of time greater than about 5 days, about 6 days, about 7 days, about 8 days, about 9 days, about 10 days, about 11 days, about 12 days, about 13 days, about 2 weeks, about 3 weeks, about 4 weeks, about 5 weeks, about 6 weeks, about 7 weeks, about 8 weeks, about 3 months, about 4 months, about 5 months, about 6 months, about 7 months, about 8 months, about 9 months, about 10 months, about 11 months, about one year, or more following administration of BMSCs attached to HyA-FMB. In embodiments, stable cartilage can resist vascularization in vivo.

Subjects

Subjects include both human and veterinary subjects, such as humans, non-human primates, cats, dogs, pigs, sheep, cows, horses, rodents, birds, and the like, which can be the recipient of the disclosed methods. A subject in need of the present methods can be those at risk of developing, or having, osteoarthritis, osteochondritis dissecans, osteochondrodysplasias, or cartilage injury. A subject in need thereof can additionally have bone damage; e.g., from osteoarthritis or accidental injury.

Osteoarthritis is a type of joint disease resultant from the breakdown of cartilage and bone within the joints. Osteoarthritis causes joint pain and stiffness, swelling and decreased range of motion.

Cartilage Injury is any injury or damage to the cartilage tissue. Cartilage injuries include tears, rips and ruptures. Cartilage injury typically occurs in the joints; e.g., knee, hip, elbow, shoulder, ankle, etc. Exemplary cartilage injuries include meniscal tears, labral tears of the hip or shoulder, talar dome lesions, and others. Cartilage injuries can occur due to accident, athletic injury, or other. In an embodiment, the mixtures of autologous naïve BMSCs with HyA-FMB are injected into cartilage lesions in animals, such as wounded horses.

Methods of the present disclosure can be utilized in the growth or repair of cartilage for subjects in need thereof. Growth or repair may include partial or complete regrowth of cartilage. Partial cartilage regrowth may include about at least 10%, 20%, 30%, 40%, 50%, 60%, 70%, 80%, 90%, 95%, 99%, or 100% regrowth of cartilage. Cartilage regrowth may be measured as a percentage of weight, or percentage of a distance, for example a cartilage length, width, diameter, or height. Repair can be measured as a percentage extension in length, height, width, diameter, or weight. Repair can further be measured as an increase in joint mobility, or subjectively, as in increase in joint comfort.

EXAMPLES

Naïve BMSC populations contain skeletal stem cells (SSCs), capable of differentiating towards a spectrum of skeletal tissues, including cartilage [reviewed in (Bianco et al., Methods Enzymol. 2006; 419:117-48). The in vitro pellet culture is currently the gold standard for demonstrating chondrogenic differentiation of hBMSCs (Johnstone and Yoo, "In vitro chondrogenesis with mammalian progenitor cells," In: Rosier R N E, C H, editor. Molecular Biology in Orthopaedics. USA: Amer Acad Orthop Surg; 2002. p. 273-87), but cells within this pellet undergo an endochondral bone formation process in vitro (Muraglia et al., J Cell Sci. 2003; 116(Pt 14):2949-55). Consequently, it is not surprising that pre-formed cartilage pellets do not generate cartilage in vivo; rather they undergo hypertrophy and mineralization (Scotti et al., Proc Natl Acad Sci USA. 2013; 110(10):3997-4002), or remodeling into a bone/marrow organ (Serafini et al., Stem Cell Res. 2014; 12(3):659-72). No protocols currently exist for formation of functional hyaline cartilage by hBMSCs in vivo (Somoza et al., Tissue Engineering Part B, Reviews. 2014; 20(6):596-608). BMSCs do not require in vitro induction to form cartilage in vivo. Naïve rabbit BMSCs form cartilage and bone when transplanted intraperitoneally within diffusion chambers (Ashton et al., Clin Orthop Relat Res. 1980(151):294-307).

Thus, naïve BMSCs seem to be primed to form cartilage, but need a "permissive" environment. In diffusion chambers, cartilage is protected from vascular invasion and endochondral ossification, both of which occur with open transplantation of both pre-differentiated BMSCs and in vitro-expanded articular chondrocytes. However, only freshly isolated or briefly expanded human articular chondrocytes have been demonstrated to form stable hyaline cartilage in vivo, see e.g., (Pelttari et al. Arthritis & Rheumatism. 2006; 54(10):3254-66).

Previous studies demonstrated that anchorage-dependent connective tissue cells bind tightly to fibrin matrix, prompting the development of fibrin microbeads (FMBs) (Gorodetsky et al., The J Invest Dermatol. 1999; 112(6):866-72). The dense FMBs made of dehydrothermally crosslinked fibrin readily support the adherence of rat fibroblastic cells and ex vivo expansion of rat BMSCs (Zangi et al., Tissue Engineering. 2006; 12(8):2343-54), and have been proposed for the use in skeletal tissue regeneration. Prior methods using fibrin-based matrices and fibrin/HyA hydrogels promoted BMSC proliferation and early chondrogenesis in vitro, but the fibrin matrix degraded too quickly to be practical for in vivo transplantation (Shainer et al., Regen Med. 2010; 5(2):255-65). Disclosed are fibrin microbeads cross-linked to hyaluronic acid, which surprisingly could be used to deliver BMSC locally such that the BMSC formed stable cartilage in vivo.

Example 1

Materials and Methods

Generation of human bone marrow stromal cells (hBMSCs). Strains of naïve hBMSCs were generated as previously described (Bianco et al., Methods Enzymol. 2006; 419:117-48). Passage 3 BMSCs were used.

Human bone surgical waste was obtained from one donor (a 1.5-year-old male with polydactyly; marrow from his right toe was used), in accordance with the NIH regulations governing the use of human subjects under protocol 94-D-0188 or OHRS Assurance #373.

Single cell suspensions of bone marrow were prepared as described previously (Bianco et al., Methods Enzymol. 2006; 419:117-48; Kuznetsov et al., Calcif Tissue Int. 1996; 59(4):265-70). Briefly, marrow fragments were scraped from human trabecular bone into α-modified Minimum Essential Medium (αMEM, Invitrogen, Grand Island, N.Y.) with a steel blade. These marrow preparations were repeatedly pipetted and passed consecutively through 16 and 19 gauge needles to break up cell aggregates. The resulting cell suspensions were filtered through a nylon cell strainer (352350, Becton Dickinson, Franklin Lakes, N.J.) to remove remaining cell aggregates.

To establish primary hBMSC cultures, $1.5-5\times10^6$ of bone marrow-derived nucleated cells were plated in 75 cm$^2$ filter cap tissue culture flasks (Corning, Inc., Corning, N.Y.) at a density of $2-6.7\times10^4$ cells/cm$^2$. Culture medium consisted of αMEM, 2 mM glutamine, 100 U/ml penicillin, 100 μg/ml streptomycin sulfate (all Invitrogen), 20% non-heat-inactivated fetal bovine serum (FBS) of a pre-selected lot (Kuznetsov et al., Transplantation. 2000; 70(12):1780-7) (Atlanta Biologicals, Inc., Lawrenceville, Ga.), dexamethasone (Sigma, St. Louis, Mo.) at $1\times10^{-8}$ M, and L-ascorbic acid phosphate magnesium salt n-hydrate (Wako, Osaka, Japan) at $10^4$ M. It was previously demonstrated that the addition of dexamethasone and L-ascorbic acid phosphate magnesium salt n-hydrate to the culture medium did not change the pattern of hBMSC in vivo differentiation following their subsequent in vivo transplantation (Kuznetsov et al., J Tissue Eng Regen Med. 2013; 7(3):226-35). Thus, these ingredients cause no "in vitro differentiation" and have been used here exclusively for the purpose of stimulating in vitro proliferation. Cultivation was performed at 37° C. in a humidified atmosphere of 5% $CO_2$ in air, with two medium replacements per week. On day 13 to 16, when BMSCs were approaching confluence, the $1^{st}$ passage was performed. Cultures were washed with Hanks' Balanced Salt Solution, and cells were detached from the culture flask with two consecutive portions of 0.05% Trypsin-EDTA (both Invitrogen). Trypsin was then inactivated by the addition of cold culture medium containing FBS. The subsequent $2^{nd}$ and $3^{rd}$ passages were performed in the same manner, 4-6 days apart, when hBMSCs approached confluence. hBMSCs of passage 3 were used for the in vivo transplantation experiments.

Preparation of fibrin microbeads (FMBs). Insoluble, stable FMBs were prepared using a dehydrothermal process of fibrin crosslinking in gel micro-drops suspended in heated oil, as previously described (Gorodetsky et al., The J Invest Dermatol. 1999; 112(6):866-72; Gorodetsky, Expert Opin Biol Ther. 2008; 8(12):1831-46) with several minor modifications.

FMBs were prepared based on protocols as described previously (Gorodetsky et al., J Invest Dematol. 1999; 112(6):866-72; reviewed in Gorodetsky, Expert Opin Biol Ther. 2008; 8(12):1831-46) with several minor modifications (Gorodetsky et al., J Invest Dematol. 1999; 112(6): 866-72; Gurevich et al., Tissue Engineering. 2002; 8(4):661-72). Frozen (−20° C.) plasma-derived fibrinogen-enriched solution referred to as paste II, containing concentrated fibrinogen (NABI Pharmaceutical, Rockville, Md.) was purified by sedimentation at 4° C. in 10% ethanol in Tris buffer with 0.02% polyoxy-ethylene-(20)-sorbitan-mono-oleate (Tween-80, Sigma, Israel). A concentrated solution of ~55-65 mg/mL of clotable, soluble protein was obtained. To form FMBs, the fibrinogen solution was mixed with thrombin/$Ca^{+2}$ from EVICEL™ kit (Omrix, Israel) to reach a final concentration of ~1-6 U/mL thrombin and 4 mM $Ca^{+2}$. Upon initiation of coagulation, the mixture was immediately poured into a heat-stable pure medium-chain-triglycerides oil (MCT, Edomim-Food Supplements, Israel) heated to reach a temperature of ~75-80° C. in a heavy-duty mixer attached to a temperature controlled heater. An emulsion with small, concentrated fibrin gel droplets floating as a suspension in the oil, was formed and stabilized within 30-45 min. Surface ventilation allowed for the initial removal of excessive humidity from the drying fibrin gel microdrops within the mixed oil. Following an additional 6-8 hrs of continuous mixing at high speed, condensed, dehydrothermally stabilized FMBs were formed in the heated oil. The resulting solid FMBs were collected and thoroughly washed to remove oil residue by a series of rinses: initially with hexan, then with acetone, followed by final rinses in an ethanol gradient of 70%, 96% and 100% (Merck-Sigma, Israel). The dried FMBs were mesh-sieved, and the size range between 105-180 μm was collected and stored at room temperature (RT) for further use. No detectable reduction of the cell binding activity of dried stored FMB following a storage of 4-5 years was noted, as determined by repeated tests for cell binding.

Modification of FMBs with hyaluronic acid to generate HyA-FMBs was performed by a covalent reaction with the crosslinker, 1-ethyl-3-(3-(dimethylamino) propyl) carbodiimide (EDC, Sigma, Israel). EDC (40 mg) was added to FMBs portion (600 mg) soaked in double distilled water in a glass container at RT and mixed thoroughly for 30 min. High molecular weight HyA with an estimated molecular size range of ~50-200,000 Da (kindly provided by BTG, Israel) (40 ml of 1mg/ml solution in distilled water) was added and the solution was mixed for additional 2 hrs in a shaker. The FMBs were allowed to settle and the supernatant was removed. The complexed HyA-FMB were rinsed in water and Ethanol (96%, 5 ml) was added to the FMBs in the shaker for 15 min to remove residual non-crosslinked HyA solution and EDC. The rinsed HyA-coated FMBs were re-suspended and rinsed for 5 min with 96% ethanol. The fluid was then removed by aspiration, and the recovered FMBs covalently coated with HyA were dried in a vacuum oven at 70° C. for 30-60 min.

In vivo transplantation assay. Naïve hBMSCs attached to FMBs were assessed by an in vivo mouse transplantation model as previously described (reviewed in Bianco et al., Methods Enzymol. 2006; 419:117-48). Transplants harvested at different time points following surgery were processed for histological examination [hematoxylin and eosin (H&E), Toluidine blue (TB)].

The differentiation potential of naïve hBMSC strains attached to various carriers was assessed by an in vivo mouse transplantation model (Krebsbach et al., Transplantation 1997; 63(8): 1059-69; Kuznetsov et al., J Bone Miner Res. 1997; 12(9): 1335-47). Three strains of immunocompromised mice were used as the transplant recipients as follows: beige/nude (Crl:NIH-Lyst$^{bg}$Foxn1$^{nu}$Btk$^{xid}$, from Charles River), NOD SCID gammaC, or NSG (Nod.Cg-Prkdc$^{scid}$IL2RG$^{tm1Wjl}$/SzJ, from Jackson Labs), and skid hairless congenic, or SHC (CB 17.Cg-Prkdc$^{scid}$Hr$^{hr}$/IcrCrl, from Charles River). The transplant procedures were performed under isoflurane anesthesia in accordance to the specifications of an institutionally approved small animal protocol. For animals in Group 1, the hBMSCs/FMBs or hBMSCs/HyA-FMBs mixtures were delivered subcutaneously through the 0.5-cm-long skin incisions, using separate 1-ml Tuberculin syringe without needles (Covidien, Mansfield, Mass.). The narrow tip of the syringe was cut away (to reduce the dead volume) such that the plunger could push the construct (having the consistency of wet snow) all the way through the syringe and under the skin. In this way, the transplants were placed 0.5-1 cm away from the incisions. Incisions were closed with a single clip. For animals in Group 2, regular surgical procedures were employed. After making a central dorsal incision, of about 2 cm long, in the back of a 8-15-wk-old female mouse, each transplant was placed, using a spatula, into a subcutaneous pocket, with up to 4 transplants per animal; an effort was made to place each transplant as far from the incision as possible. The incision was closed with three or four 9-mm steel wound clips (Roboz Surgical Instrument Co., Inc., Rockville, Md.).

The transplants were harvested at different time points following surgery, ranging from 8 to 28 wks. The transplants were fixed overnight at 4° C. with freshly prepared cold 4% phosphate-buffered formalin (Sigma), and then demineralized with 10% EDTA, pH 8.0 (Quality Biologicals, Inc., Gaithersburg, Md.) at 4° C. The transplants were then cut into parallel pieces and embedded in paraffin. Serial 6 μm thick sections were prepared such that large cross-section areas of the transplants were represented on the slides. The sections were deparaffinized, hydrated, and stained with either Hematoxylin and Eosin (H&E), or Toluidine Blue (TB, which metachromatically stains cartilage purple), or by immunostaining. Histological examination was performed on stained sections with photomicrograph documentation with a Zeiss Axioplan 2 microscope equipped with an AxioCam HRc camera (Carl Zeiss, Inc., Thornwood, N.Y.).

New bone and cartilage formation score. The extent of bone formation within each transplant was scored with a semi-quantitative, exponential scale from 0-4 as described previously, and a similar scale to score cartilage formation was developed that also took into account the degree of cartilage maturation.

The extent of bone formation within each transplant was scored with a semi-quantitative, exponential scale from 0 to 4 in a manner described previously (Mankani et al., Biotechnol Bioeng. 2001; 72(1) 96-107). Score 0 indicates no bone formation; score 1 for minimal bone formation where a single or a few bone trabeculae could be seen in one or a few sections; score 2 for low bone formation with multiple bone trabeculae present in several areas of some sections but the new osseous tissue occupies only a small portion of the sections; score 3 for moderate bone formation where bone occupies a significant area of the section but does not exceed one half of the area of most sections; score 4 for abundant bone formation, where osseous tissue occupies greater than one half of each section of the transplant. When the bone scores based on this scale were compared to histomorphometric measurements of relevant tissue sections, a high correlation was previously reported between the bone score and the square root of the fraction of bone area in the sections to total area of the transplant (Mankani et al., Biotechnol Bioeng. 2001; 72(1) 96-107).

For the current study, a similar semi-quantitative exponential scale was developed to score the formation of cartilage within each transplant. Scoring cartilage, however, turned out to be more complicated since the maturity of new chondrogenic tissues had to be taken into account in addition to the relative prevalence of the areas occupied by cartilage. Cartilage maturity could be roughly estimated based on the intensity of metachromasia in sections stained with Toluidine Blue. Altogether, the following, exponential scale from 0 to 4 was developed:

Score 0 for no cartilage formation; score 1 stands for minimal cartilage formation with just a single or a few small areas in one or in a few sections; score 2, for low cartilage formation, in which cartilaginous areas were observed in several areas of some sections but they occupied only a small area of the sections; alternatively, cartilage occupied up to one half of most sections but, in significant parts of it, levels of metachromasia was low; score 3 for moderate cartilage formation, in which cartilaginous areas occupied a significant area but of less than one half in most sections, or alternatively, where cartilage occupied greater than one half of the area of most sections, but, in significant parts of it the levels of metachromasia were low; score 4 for abundant cartilage with mature cartilaginous areas, where cartilage demonstrating high levels of metachromasia occupied greater than one half of each section.

Immunostaining for Type II collagen, Type X collagen, and human mitochondria. Immunostaining was performed on deparaffinized and rehydrated sections using standard procedures.

Immunostaining was performed on deparaffinized and rehydrated sections. The following specific primary antibodies were used: anti-pan-mammalian Type II collagen (#34712, Abcam, Cambridge, Mass.) at 1:200 dilution; anti-human Type X collagen (rabbit polyclonal antibody created previously) at 1:400 dilution; anti-human mitochondria (MAB 1273, Millipore Corp) at 1:50 dilution.

For staining Types II and X collagens, enzymatic retrieval was performed with hyaluronidase (#H3884, Sigma) at 2 mg/ml in PBS, for 1 h at 37° C. Endogenous peroxidase was blocked for 10 min by Dual Block (#S2003, Dako Glostrup, Denmark). Specific primary antibodies were diluted in 10% goat serum in PBS; the first two antibodies were incubated overnight at 4° C., while the anti-Type X collagen antibody was incubated for 1 h at RT. Before incubation with the anti-human mitochondria antibody, heat retrieval was performed at 70° C. for 30 min using the Uni-Trieve solution (#NB325, Innovex Biosciences Inc, Richmond, Calif.), followed by overnight incubation with the antibody at 4° C.

For all sections, Super Picture HRP polymer Conjugate (#878963, Invitrogen) was applied for 10 min as the secondary antibody. Chromogenic staining was then performed by applying 3-amino-9-ethylcarbazole (AEC) or 3, 3-diaminobenzidine (DAB). In all studies, non-immune immunoglobulins of the same isotype as the primary antibodies were used as negative controls.

Statistical Analyses. When applicable, a two tailed Mann-Whitney U test was utilized.

Vehicles used and their loading with naïve hBMSCs.

In Group 1 mice (FIG. 1B), modified FMBs covalently coated with HyA (HyA-FMBs) were used as the transplantation carrier, and compared with unmodified FMBs. Loading with hBMSCs was performed in as described above (small incision and injection).

Figure 3A:
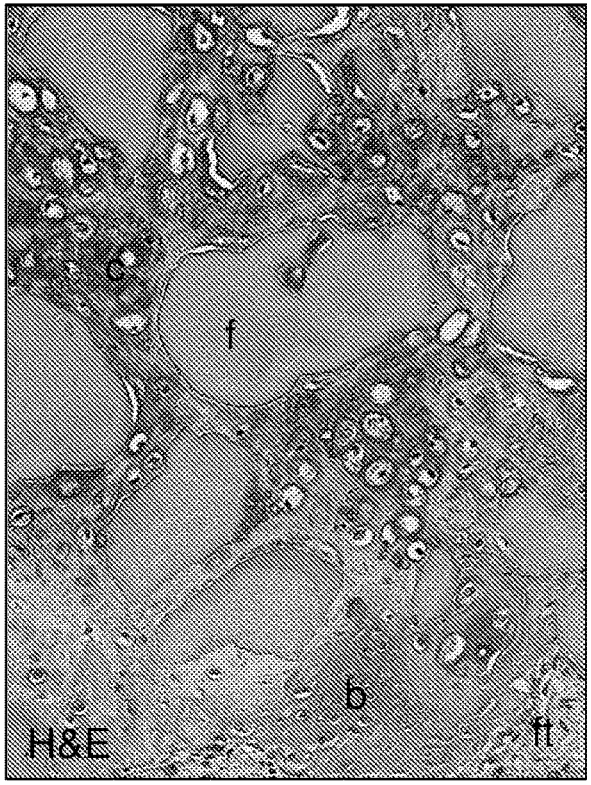
FIGS. 3A-3F: Histological and immunohistochemical analysis of transplants harvested at 8 weeks (wks). Transplants in NSG mice showed strong basophilic staining of cartilaginous areas by H&E in (FIG. 3A) and substantial metachromasia with TB in (FIG. 3B). HyA-FMB transplants from SHC mice were less mature, as indicated by lower intensity of TB staining (immature cartilage) in (FIG. 3C). Empty HyA-FMBs shown in (FIG. 3D), exhibited no sign of cartilage formation, with only sparse fibrous tissue surrounding the microbeads. There was very limited but detectable staining for Type X collagen (FIG. 3E), compared with the staining obtained with a non-immune immunoglobulin of the same isotype shown in (FIG. 3F). b=bone; c=cartilage; f=residual fibrin microbeads (FMBs); ft=fibrous tissue; H&E=hematoxylin and eosin; ic=immature cartilage; NSG=immunocompromised mouse strain; SHC=immunocompromised mouse strain; TB=Toluidine blue (metachromatic staining of cartilage matrix); Anti-COL X=staining with an antibody against Type X collagen; Isotype Control=staining with a non-immune immunoglobulin with the same isotype as the anti-Type X antibody.
Figure 3B:
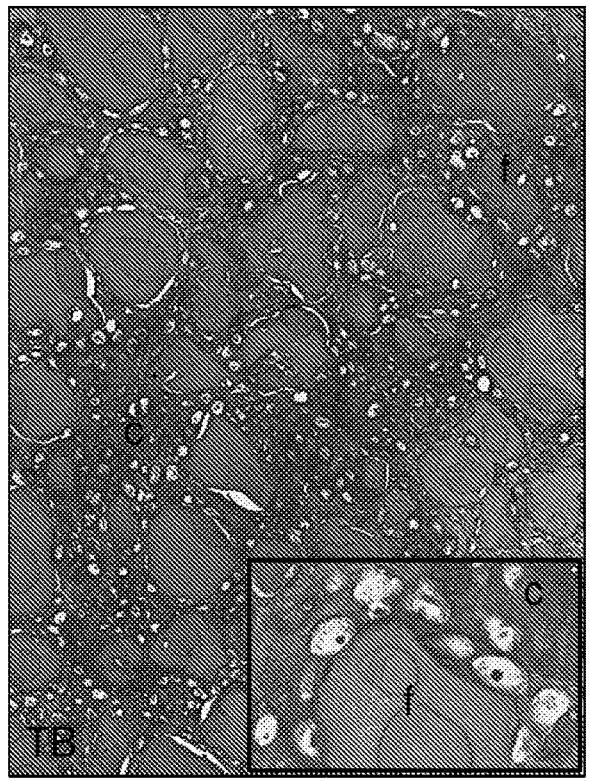
Figure 3C:
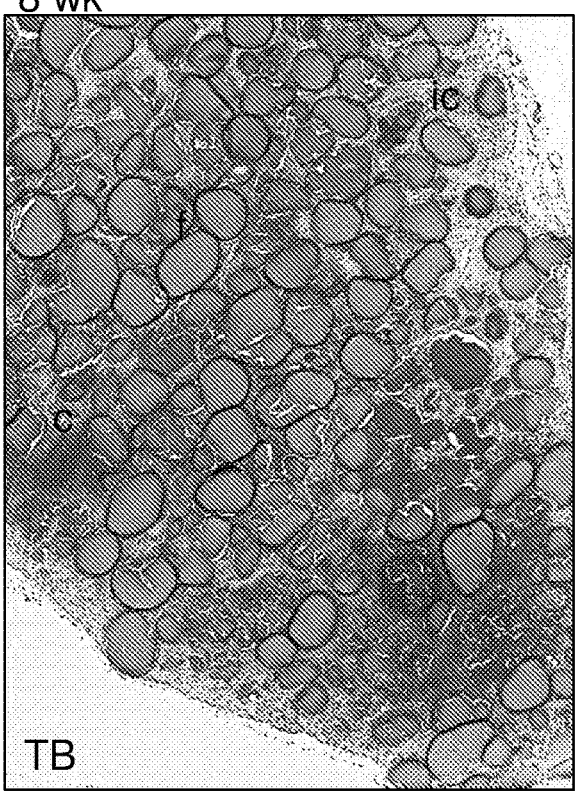
Figure 3D:

In Group 2 mice (FIG. 2, FIG. 5A-FIG. 5D), HyA-FMBs were transplanted into 2 different strains of immunodeficient mice (NSG and SHC) using a standard surgical approach as described above. In this experiment, empty scaffolds, devoid of cells, were also used in NSG mice (FIG. 3D).

Example 2

FMB Modification Enhanced Stable Cartilage Formation

Figure 1B:
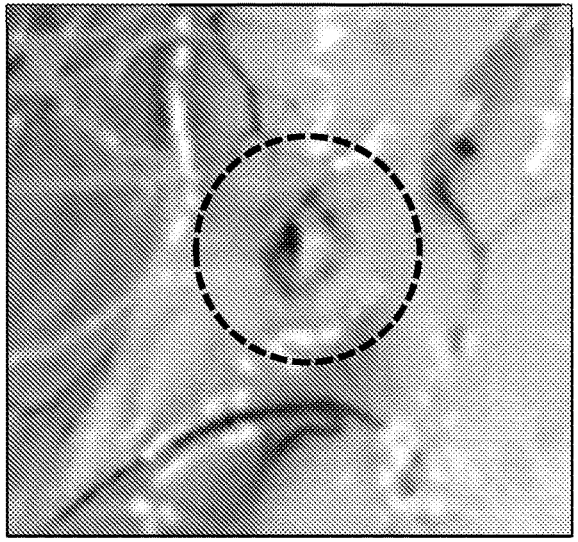
Figure 1B:
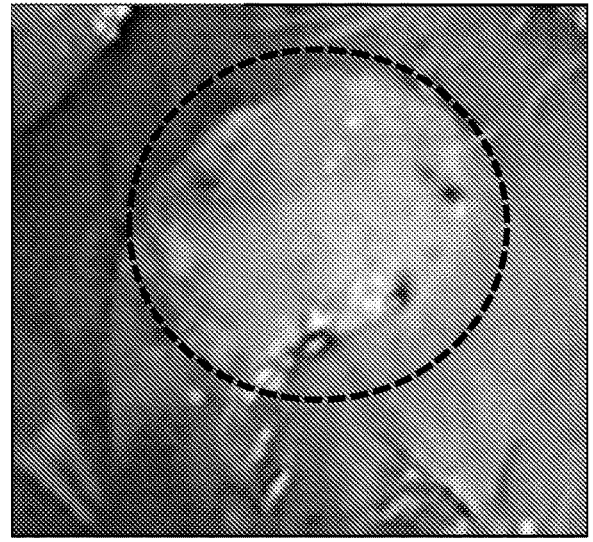

FMBs were then crosslinked to HyA (HyA-FMBs) and compared with unmodified FMBs. All transplants were generated in NSG mice, and harvested after 19 weeks (Group 1, FIG. 1B). hBMSC/FMB transplants were small and dark, with a greyish-pinkish tinge (FIG. 1C). In 3 of 5 hBMSC/FMB transplants, a small amount of cartilage was observed (score 1.2±1.1) (FIG. 1B). hBMSC/HyA-FMB transplants were large, white, glossy in appearance, and harder than hBMSC/FMB transplants (FIG. 1D). Cartilage was found in 5/5 transplants at a statistically higher level than in hBMSC/FMB transplants (FIG. 1A, 3.0±0.7 vs. 1.2±1.1, p=0.0317). Vast fields of cartilage contained chondrocytes in small lacunae surrounded by ECM with strong basophilic staining with H&E (FIG. 1G), and intensely metachromatic staining with TB (FIG. 1H). Substantial amounts of bone were also found in all transplants (10 of 10), but not statistically different between the two types (FIG. 1B, 2.2±0.8 vs. 3.0±0.0, p=0.1667). Bone trabeculae were located at the periphery of the transplants (FIGS. 1E and 1F), and surrounded areas of hematopoiesis (FIGS. 1E and 1F).

Example 3

Time Course of Cartilage Formation in HyA-FMB Transplants

Figure 3E:
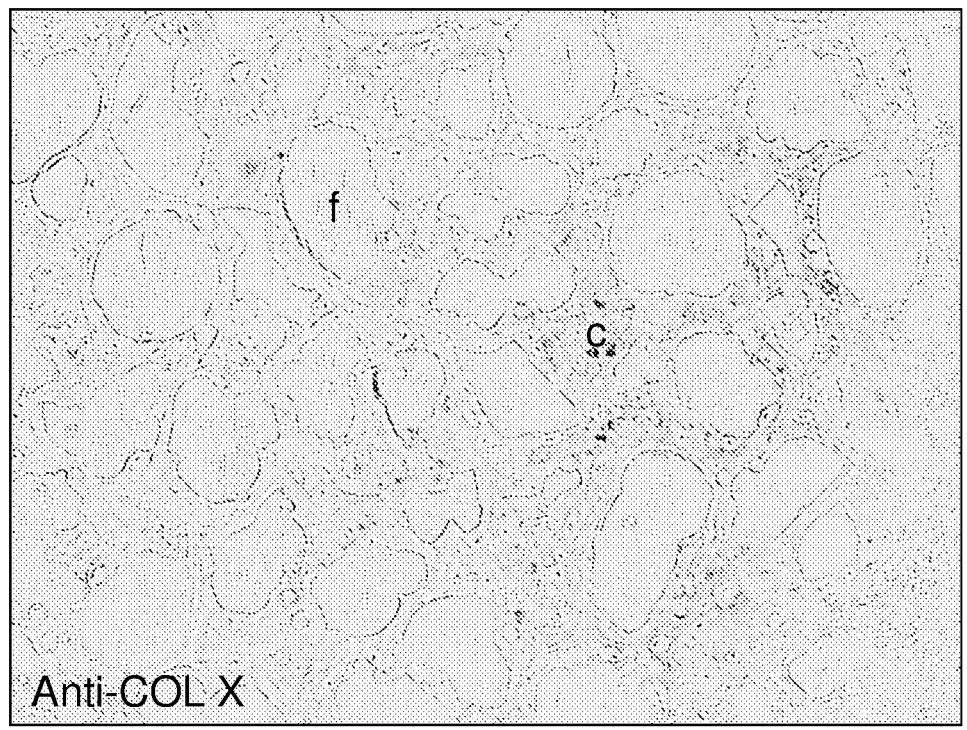
Figure 3F:
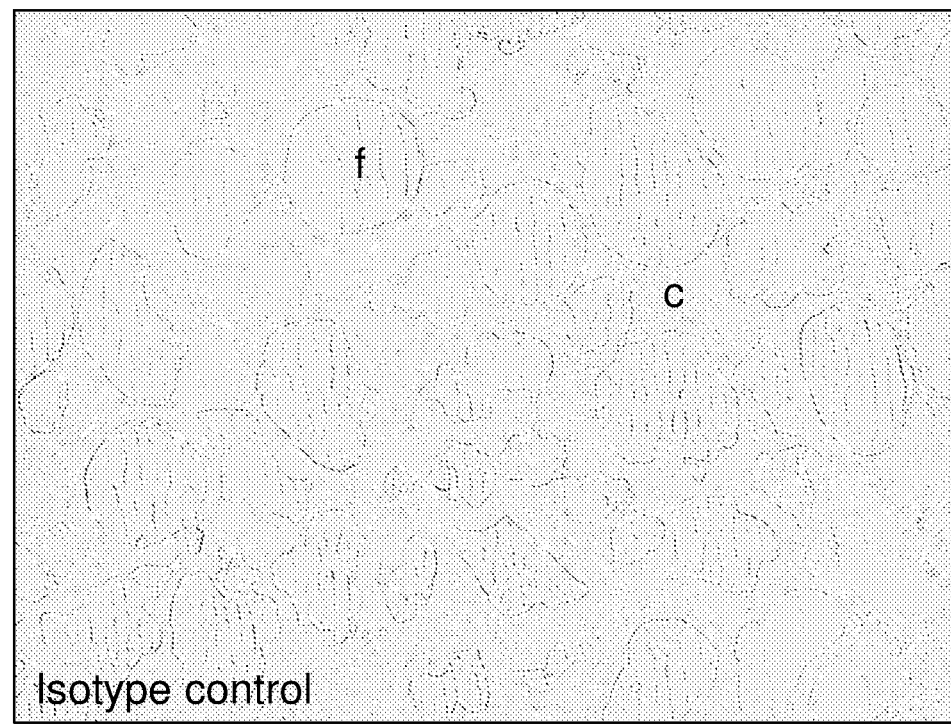

In Group 2, hBMSCs/HyA-FMBs were transplanted into NSG and SHC (another congenic highly immunocompromised) mice and harvested at 8, 16, and 28 wks (FIG. 2). At 8 wks, all transplants were recovered, and had undergone shrinkage, but were well separated from surrounding tissues. SHC hBMSC/HyA-FMB transplants demonstrated only minimal immature cartilage (score 0-1), but no bone (FIGS. 2 and 3C) at this time point. NSG BMSC/HyA-FMB transplants displayed some positive staining for Type X collagen (FIGS. 3E and 3F). In these positive areas, some cells resembled hypertrophic chondrocytes (increased size, pyknotic nuclei, fragmented cytoplasm. Most of the cartilage in SHC transplants did not stain for Type X collagen and demonstrated no morphological features of hypertrophic cartilage.

Figure 4A:
FIGS. 4A-4F: Subcutaneous transplantation of naïve hBMSCs with FMBs with covalently bound hyaluronic acid (HyA-FMBs) into immunocompromised mice (NSG and SHC strains) for 16 wks. At 16 wks, substantial cartilage (score 3) and some bone (score 1) were formed in hBMSC/HyA-FMBs in NSG mice (FIGS. 4A and 4B); less cartilage (score 2) was formed in SHC mice (FIG. 4C). Small areas of fibrous tissue were noted, along with large fields of basophilic staining (FIG. 4A), that stained intensely with TB (FIG. 4C), although cartilage formed in SHC mice was slightly less mature than in NSG (FIG. 4C). Cartilaginous areas stained positively with antibodies against Type II Collagen (FIG. 4D), but did not stain with antibodies against Type X Collagen (FIG. 4E). A non-immune immunoglobulin of the same isotype as the anti-Type II and anti-Type X antibodies elicited no staining (FIG. 4F). c=cartilage, f=residual fibrin microbeads (FMBs), ft—fibrous tissue, H&E=hematoxylin and eosin, ic=immature cartilage, NSG=immunocompromised mouse strain, SHC=immunocompromised mouse strain, TB=toluidine blue (metachromatic staining of cartilage matrix), Anti-COL II=staining with an antibody against Type II collagen, Anti-COL X=staining with an antibody against Type X collagen, Isotype Control=Staining with a non-immune immunoglobulin with the same isotype as the anti-Type II and anti-Type X antibodies.
Figure 4B:
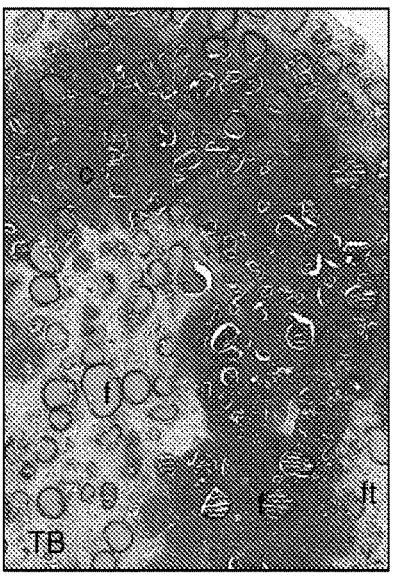
Figure 4C:
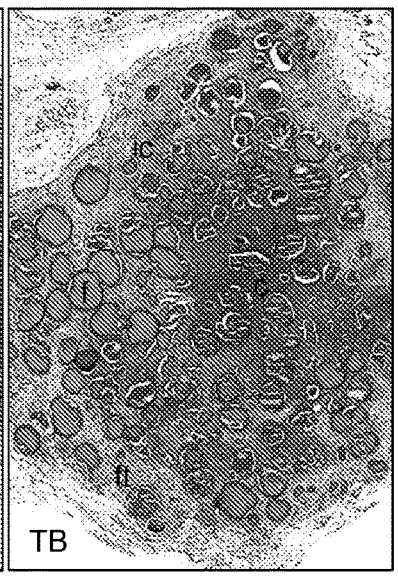
Figure 4D:
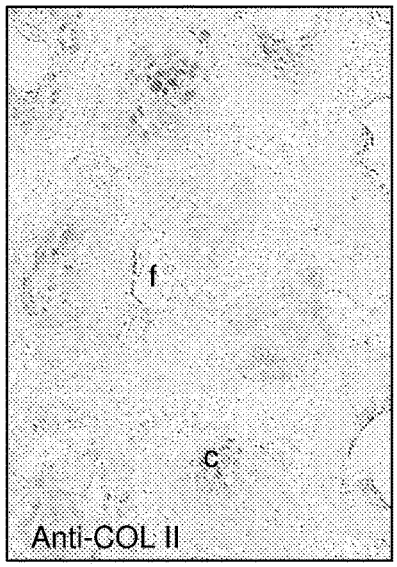
Figure 4E:
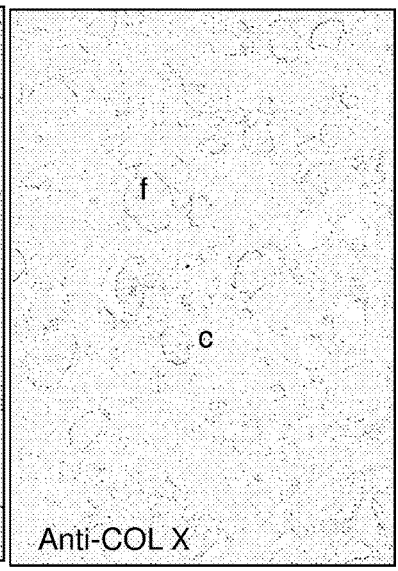
Figure 4F:
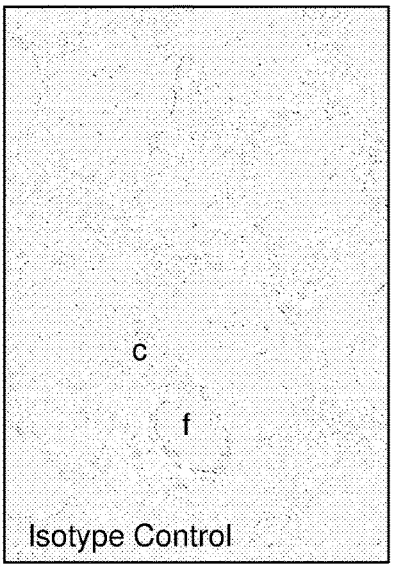

At 16 wks, transplants from both mouse strains were white, glossy and hard. In NSG BMSC/HyA-FMB transplants, significant areas of mature cartilage (score 3) were formed (FIGS. 2, 4A and 4B). In SHC BMSC/HyA-FMB transplants, less mature cartilage (score 2) was formed (FIGS. 2 and 4C). In NSG transplants, ECM surrounding chondrocytes demonstrated moderate to strong staining for Type II collagen (FIG. 4D, 4F is the isotype control). The vast majority of the newly formed cartilage showed no immunoreactivity for Type X collagen (FIG. 4E, 4F is the isotype control). Similar results were found in SHC transplants.

Figure 5E:
Figure 5F:
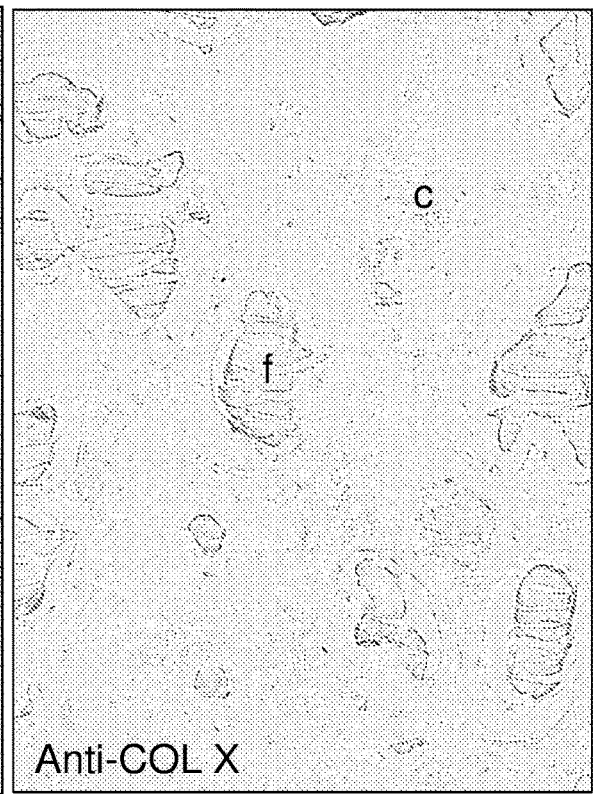

At 28 wks, both NSG and SHC transplants persisted, as did their white, glossy, pearl-like appearance (FIG. 2 and insets, FIGS. 5A and 5C), and their rigid consistency. Cartilage occupied almost the entire sections of these transplants (NSG score 3, SHC score 4; FIG. 2 and FIG. 5A-5D). Narrow strips of fibrous tissue and thin, isolated bone trabeculae were observed at the periphery of the transplants (insets, FIGS. 5B and 5D). In NSG transplants, the new ECM displayed moderate to strong positive staining for Type II collagen compared with the isotype control (FIGS. 5E and 5H), with similar results for SHC transplants. Throughout the entire NSG and SHC 28-wk transplants, staining for Type X collagen was negative (SHC transplants shown in FIG. 5F). Residual FMBs persisted in all transplants (FIGS. 5A and 5D).

Taken together, stable, hyaline-like cartilage persisted, or expanded, up to the latest time point of 28 wks. At the same time, differences in transplant development were observed between recipient mouse lines used in this experiment (FIG. 2).

Example 4

Origin of Cartilage in the Transplants

Figure 5G:
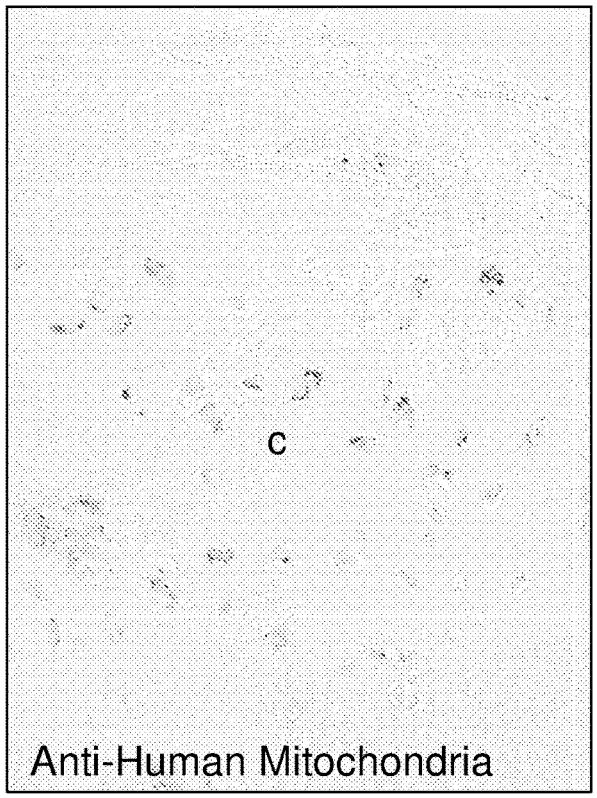
Figure 5H:
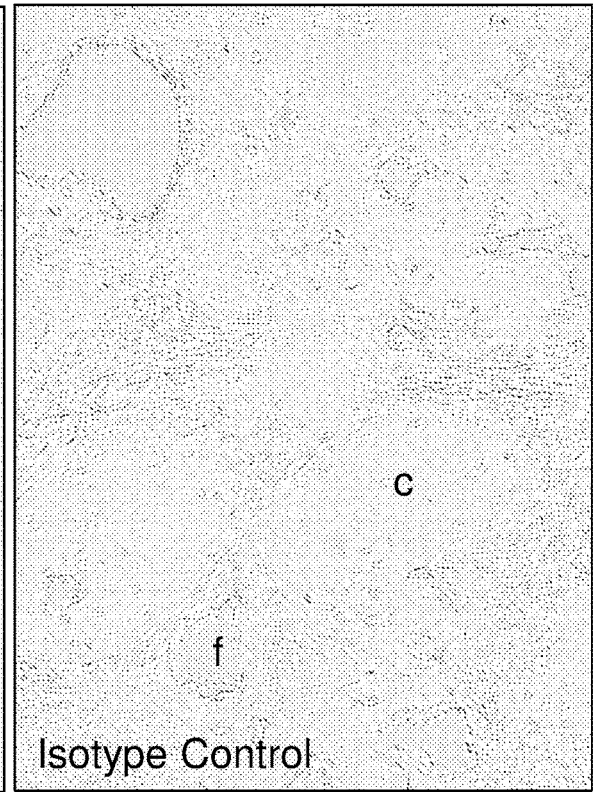

The donor origin of cartilage was determined in NSG 28-wk transplants stained with an antibody specific for human mitochondria. Positive staining (FIG. 5G) demonstrated the human origin of the chondrocytes compared with the isotype control (FIG. 5H). When empty FMBs (without hBMSCs) were transplanted, there was no trace of FMBs at 8 wks, whereas empty HyA-FMBs could still be found (FIG. 2). The empty HyA-FMB transplants consisted of large, non-resorbed FMBs, sparsely populated with fibrous tissue with no cartilage (FIG. 3D). By 16 wks, neither empty FMBs, nor empty HyA-FMBs were found (FIG. 2).

In the examples above, transplants of both unmodified FMBs and HyA-FMBs with naïve hBMSC resulted in generation of stable, glossy-white, resilient tissues in vivo, histologically similar to hyaline cartilage. At the earlier time points (8 wks), peripheral regions of cartilaginous areas were less mature, or demonstrated hypertrophic chondrocyte morphology and stained positively for Type X collagen. These areas were considerably smaller than the vast Type X collagen-negative areas. Importantly, Type X collagen-positive areas diminished between 8 to 16 wks, and totally disappeared by 28 wks. Immunostaining for human mitochondria verified the human origin of the chondrocytes, even at 28 wks (~0.5 yrs), suggesting that the human cartilage had no tendency to become hypertrophic, to undergo endochondral ossification, or to be invaded by blood vessels. The mature-looking human cartilage not only persisted, but sometimes significantly expanded, occupying almost the entire area of the transplants.

The constructs supporting stable cartilage formation were transplanted following a 90-minute co-incubation of HyA-FMBs with naïve BMSCs. With HyA-FMBs, only minimal bone was formed in SHC mice, while more osteogenesis occurred in NSG mice. These results highlight differences between mouse strains. In NSG mice, moderate cartilage was formed by the earliest time point (8 wks); it stayed relatively stable, unchanged or only slightly increased by 16 and 28 wks. In SHC mice, mature cartilage formation was minimal at 8 wks, was low at 16 wks, and reached its highest score of 4, by 28 wks.

While some types of cartilage (nasal and auricular) are located subcutaneously, this location is considered to be non-permissive for development and persistence of hyaline cartilage. For example, when non-hypertrophic chondrocytes differentiated from pluripotent stem cells were transplanted subcutaneously, mineralized cartilage and bone were formed within 8 wks, leading the authors to conclude that the subcutaneous microenvironment is incompatible with maintenance of stable cartilage (Craft et al, Nat Biotechnol. 2015; 33(6):638-45). Other studies, using human articular chondrocytes, reached the same conclusion. However, fresh or low passage human articular chondrocytes do form stable cartilage subcutaneously, e.g., see Pelttari et al. Arthritis & Rheumatism. 2006; 54(10):3254-66, the very same cells that had some partial success when used clinically. For therapeutically meaningful cartilage regeneration, cells must produce stable cartilage, resistant to vascularization and calcification, even at hostile ectopic sites.

Example 5

Repair of an Osteochondral Defect in Additional Murine Models

Additional models were used to demonstrate that intra-articular implantation hBMSCs attached to FMB-HyA leads to superior cartilage defect healing in murine models, as compared to untreated defects and defects treated with FMB-HyA alone.

A. Additional Results in the NSG Mouse

The NSG mouse trochlear osteochondral defect supports the implantation of FMB-HyA and BMSCs. This model can be used to study early repair, and this surgical defect procedure is a feasible model for studying long term osteochondral repair outcomes.

This intra-articular osteochondral mouse defect was established (FIGS. 6A-6D). The mouse was placed in the supine position, and a skin incision was made with scissors over the medial aspect of the mouse knee. A 5 mm-10 mm incision was made on the medial aspect of the mouse knee capsule, and the patella was gently dislocated laterally, exposing the trochlea. A 0.5 mm micro drill was used to create an osteochondral defect in the trochlea of the distal mouse femur to a depth of 1.5 to 2 mm. A 0.5 mm micro curette was used to apply scaffold material to the defect and secondarily to pressurize the scaffold and cellular material into the defect. A layer of fibrin glue was used for retaining of the scaffold/cell construct in the defect during the engraftment process. The patella and knee extensor mechanism was then relocated, and the skin is closed with a combination of animal skin adhesive (Vetbond, 3M, St. Paul, Minn.) and 6-0 nylon suture material.

Due to anatomic size constraints, mice have not been well established as an ideal preclinical model for cartilage regeneration. Despite this, mice offer advantages when compared with rats in this regard. For example, there are many cartilage disease models available in mice, they are easier to maintain and less expensive, they have superior immunosuppressed strains to better support xenografts, and they well proven to support subcutaneous cartilage growth models (Ahern et al., Osteoarthr Cartil. 2009; 17(6):705-713. doi:10.1016/j.joca.2008.11.008; Cook et al., Bone Joint Res. 2014; 3(4):89-94. doi:10.1302/2046-3758.34.2000238). The NSG mouse trochlear osteochondral defect can support the implantation of FMB-HyA and BMSCs as a model for early repair, and this surgical defect procedure is a feasible model for studying long term osteochondral repair outcomes The mouse was placed in the supine position, and a skin incision was made with scissors over the medial aspect of the mouse knee. A 5 mm-10 mm incision was made on the medial aspect of the mouse knee capsule, and the patella was gently dislocated laterally, exposing the trochlea. A 0.5 mm micro drill was used to create an osteochondral defect in the trochlea of the distal mouse femur to a depth of 1.5 to 2 mm. A 0.5 mm micro curette was used to apply scaffold material to the defect and secondarily to pressurize the scaffold and cellular material into the defect. A layer of fibrin glue was used, retaining the scaffold/cell construct in the defect during the engraftment process. The patella and knee extensor mechanism was then relocated, and the skin closed with a combination of animal skin adhesive (Vetbond, 3M, St. Paul, Minn.) and 6-0 nylon suture material.

1. Short Term NSG Mouse Osteochondral Defect Repair

After cells were attached to HyA-FMB, the surgical area was prepared within a biosafety hood, for maintaining sterility and protecting the immunocompromised animals. Animals were anesthetized with 2-5% isoflurane, and the implantation procedure was carried out. After the procedure was completed, each animal was treated with Buprenorphine (Animalgesics Labs, Millersville, Md.) for pain control. During recovery, animals were returned to their cages and allowed to ambulate normally. Animal euthanasia timepoints are described in Table 1

TABLE 1

NSG Mice Short-Term Osteochondral Defect Experiment*

| Euthanasia Timepoint | Fibrin Glue + FMB-HyA + hBMSCs | FMB-HyA + hBMSCs | Fibrin Glue + hBMSCs | No Treatment |
|---|---|---|---|---|
| 1 day | 1 | 1 | 1 | 1 |
| 5 days | 1 | 1 | 1 | 1 |
| 1 week | 1 | 1 | 1 | 1 |
| Group Total | 3 | 3 | 3 | 3 |

*Numbers given knees/procedures

2. Long Term NSG Mouse Osteochondral Repair

Long term NSG mouse osteochondral repair experiments established the feasibility of this model for true structural joint repair and tissue regeneration. Longer-term timepoints were used (Table 2).

TABLE 2

NSG Mice Long-Term Osteochondral Defect Experiment*

| Euthenasia Timepoint | Fibrin Glue + FMB-HyA + hBMSCs | FMB-HyA + hBMSCs | Fibrin Glue + hBMSCs | No Treatment |
|---|---|---|---|---|
| 8 weeks | 4 | 4 | 2 | 2 |
| 16 week | 4 | 4 | 2 | 2 |
| Group Total | 8 | 8 | 4 | 4 |

*Numbers given knees/procedures

Figure 7:
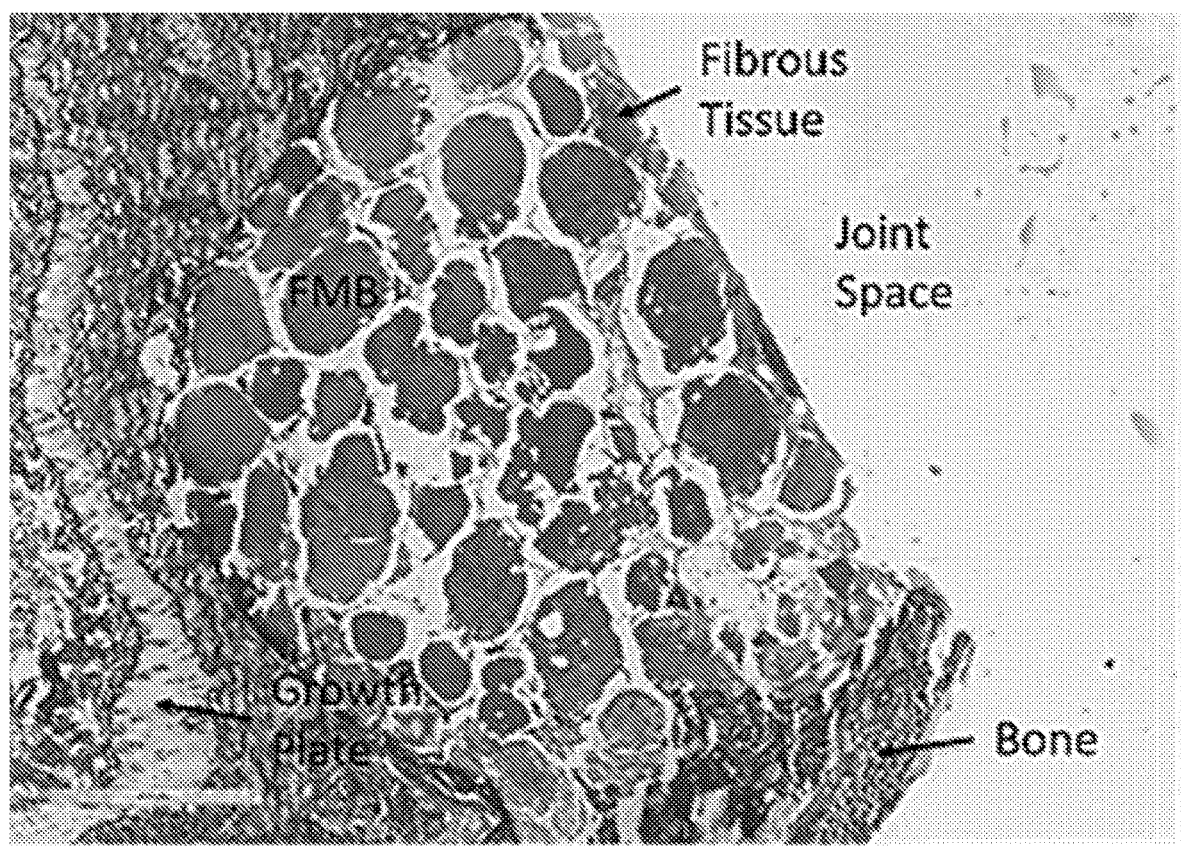
FIG. 7: Cryohistology of Osteochondral repair with FMB-HyA+hBMSCs at 5 days post-procedure.
Figure 8:
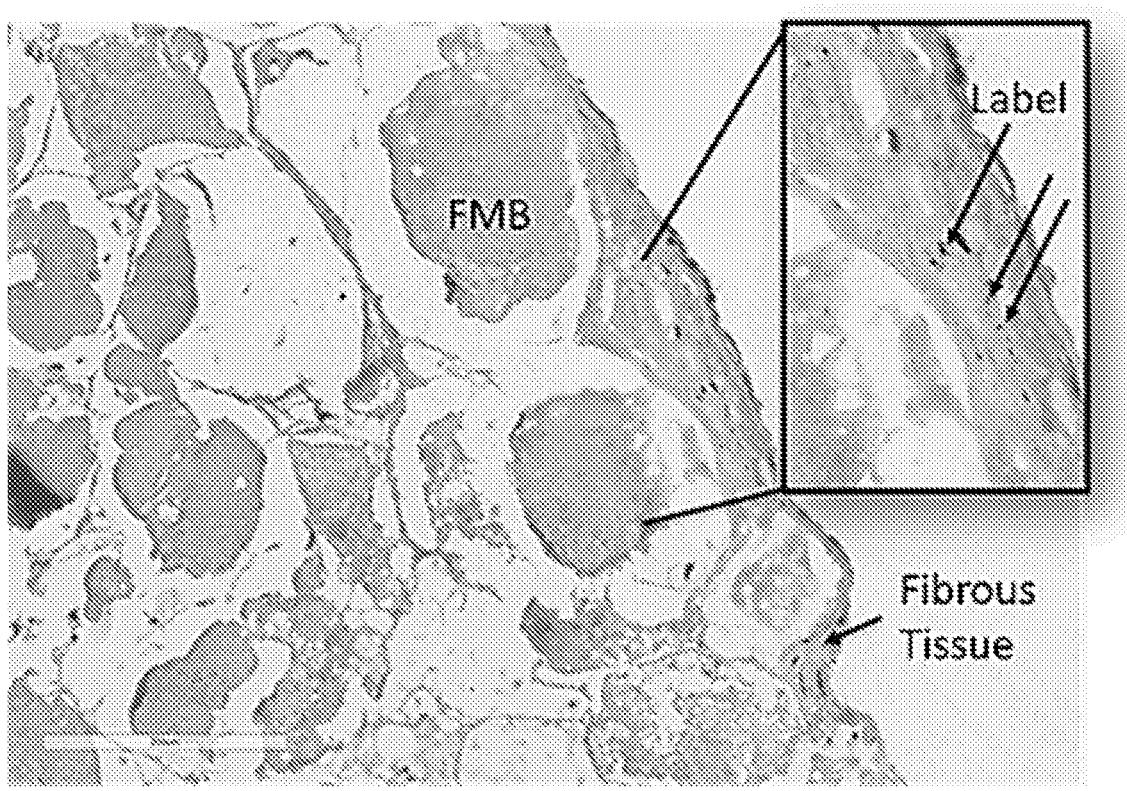
FIG. 8: Cryohistology Prussian Blue Staining of Osteochondral Defect.

The NSG mice tolerated the procedure well and had no mobility deficits post-operatively. H&E Cryohistology at 5 days demonstrated retention of FMB-HyA in the defect and fibrous overgrowth at joint surface (FIG. 7). Iron nanoparticle labeled hBMSC integration into developing fibrous tissue at joint surface was visible on Prussian Blue Staining (FIG. 8). No difference in FMB-HyA or hBMSC retention was noted between defects with and without fibrin glue overlay.

B. SRG Rat Osteochondral Defect Model

The rat model of the osteochondral defect has been well established for testing of defect repair/regenerative methods. Some immunocomprimised rat models, such as the RNU rat, have residual immunity and increased NK cell activity. The Hera Biolabs SRG rat is a newly developed RAG2/IL2R double knock-out that displays immunity analogous to the NSG mouse.

Methods

Trochlear Osteochondral defects and subsequent repairs were conducted as described above. The animal cohorts was structured as follows:

SRG Rat Intra-articular defect mid-term

| Euthanasia Timepoint | Subcutaneous FMB-Hya + hBMSC | Intra-articular FMB-Hya + hBMSC | Intra-articular FMB-Hya Only | Intra-articular hBMCS Only | No Treatment |
|---|---|---|---|---|---|
| 8 weeks | 4 | 6 | 1 | 2 | 1 |
| 12 weeks | 4 | 6 | 1 | 2 | 1 |
| Group Total | 8 | 12 | 2 | 4 | 2 |

Design of SRG Rat Intrarticular osteochondral defect Experimental and Control Groups and Euthanasia/Analysis Timepoints; numbers represent implants/defects This model was used to validate the claimed methods.

In view of the many possible embodiments to which the principles of the disclosure may be applied, it should be recognized that the illustrated embodiments are only examples of the disclosure and should not be taken as limiting the scope of the invention. Rather, the scope of the disclosure is defined by the following claims. We therefore claim as our invention all that comes within the scope and spirit of these claims.

We claim:

1. A method for promoting cartilage growth and/or repair in a subject, comprising
   administering locally to a site in need of cartilage growth and/or repair in the subject, bone marrow stromal cells attached to fibrin microbeads comprising crosslinked hyaluronic acid;
   thereby producing stable cartilage locally at the site in the subject.

2. The method of claim 1, wherein the cartilage is stable for more than 5 weeks after administering the bone marrow stromal cells.

3. The method of claim 1, wherein the cartilage is stable for more than 8 weeks after administering the bone marrow stromal cells.

4. The method of claim 1, wherein the cartilage is hyaline-like cartilage.

5. The method of claim 1, wherein the cartilage expresses type II collagen, aggrecan, or both.

6. The method of claim 1, wherein the cartilage does not express type X collagen beyond 28 weeks after administering the bone marrow stromal cells attached to the fibrin beads.

7. The method of claim 1, wherein the bone marrow stromal cells express one or more of CD29, CD73, CD90, CD140b, and CD146.

8. The method of claim 1, wherein administration is via injection to the site.

9. The method of claim 8, wherein the injection is intra-articular or trans-osseous.

10. The method of claim 1, wherein administration is via a minimally invasive surgical procedure.

11. The method of claim 1, wherein the administration is to a knee, shoulder, wrist or hip of the subject.

12. The method of claim 1, wherein the subject is at risk of developing, or has, osteoarthritis, osteochondritis dissecans, osteochondrodysplasias, or cartilage injury.

13. The method of claim 1, wherein the subject has bone damage.

14. The method of claim 1, further comprising,
producing the fibrin microbeads by mixing dense fibrin gel in heated oil to a temperature of 60-80° C., thereby producing a suspension; and
mixing the suspension for 4-10 hrs, thereby producing the fibrin microbeads.

15. The method of claim 1, wherein the fibrin microbeads do not comprise methacrylic anhydride.

16. The method of claim 1, wherein the fibrin microbeads comprise 70% fibrin or more.

17. The method of claim 1, wherein the fibrin microbeads have a density of greater than 1.15 g/mL.

18. The method of claim 1, wherein the fibrin microbeads have a density of 1.25-1.35 g/mL.

19. The method of claim 1, wherein the fibrin microbeads have a mean diameter of 80-250 μm.

20. The method of claim 1, wherein the hyaluronic acid is crosslinked to the fibrin microbeads by 1-ethyl-3-(3-(dimethylamino) propyl) carbodiimide (EDC), divinyl sulfone (DVS), glutaraldehyde (GTA), and/or poly(ethylene glycol) diglycidyl ether (EX 810).

21. The method of claim 1, wherein the hyaluronic acid has an estimated size range of about 50,000-200,000 Da.

22. The method of claim 1, wherein the subject is human.

23. The method of claim 1, wherein the bone marrow stromal cells are autologous.

24. The method of claim 22, wherein the bone marrow stromal cells are human bone marrow stromal cells.

25. The method of claim 1, further comprising administering an anti-inflammatory agent to the subject.

26. The method of claim 25, wherein the anti-inflammatory agent is a non-steroidal anti-inflammatory agent.

27. The method of claim 13, wherein the bone damage is microtrauma, a microfracture, or a subchondral fracture.

* * * * *